US012714573B2

(12) United States Patent
Predick

(10) Patent No.: US 12,714,573 B2
(45) Date of Patent: Aug. 25, 2026

(54) EXPANDABLE IMPLANT ASSEMBLY WITH MODULAR ENDPLATES

(71) Applicant: LIFE SPINE, INC., Huntley, IL (US)

(72) Inventor: Daniel Predick, Wheat Ridge, CO (US)

(73) Assignee: LIFE SPINE, INC., Huntley, IL (US)

(*) Notice: Subject to any disclaimer, the term of this patent is extended or adjusted under 35 U.S.C. 154(b) by 128 days.

(21) Appl. No.: 18/637,048

(22) Filed: Apr. 16, 2024

(65) Prior Publication Data

US 2024/0341975 A1 Oct. 17, 2024

Related U.S. Application Data

(60) Provisional application No. 63/496,537, filed on Apr. 17, 2023.

(51) Int. Cl.
*A61F 2/44* (2006.01)
*A61F 2/30* (2006.01)

(52) U.S. Cl.
CPC .......... *A61F 2/447* (2013.01); *A61F 2/30734* (2013.01); *A61F 2/30771* (2013.01); *A61F 2002/30326* (2013.01); *A61F 2002/30331* (2013.01); *A61F 2002/30429* (2013.01); *A61F 2002/30538* (2013.01); *A61F 2002/30736* (2013.01); *A61F 2002/30784* (2013.01); *A61F 2002/3092* (2013.01); *A61F 2002/3093* (2013.01)

(58) Field of Classification Search
CPC .................. A61F 2/447; A61F 2/30734; A61F 2002/30326; A61F 2002/30538; A61F 2/4425; A61F 2002/443; A61F 2/4455; A61F 2/4405; A61F 2/44
USPC ..................... 623/17.11–17.16; 606/246–249
See application file for complete search history.

(56) References Cited

U.S. PATENT DOCUMENTS

| | | | |
|---|---|---|---|
| 8,377,140 | B2 | 2/2013 | Defalco et al. |
| 9,622,878 | B2 | 4/2017 | Grotz |
| 10,369,009 | B2 | 8/2019 | Joly et al. |
| 10,413,427 | B2 | 9/2019 | Trieu |
| 10,856,997 | B2 | 12/2020 | Cowan et al. |
| 10,888,430 | B2 | 1/2021 | Kieser et al. |

(Continued)

FOREIGN PATENT DOCUMENTS

WO WO-2017/039596 A1 3/2017

OTHER PUBLICATIONS

International Search Report on PCT/US2024/024781 dated Jul. 17, 2024.

*Primary Examiner* — Eduardo C Robert
*Assistant Examiner* — Tara Rose E Carter
(74) *Attorney, Agent, or Firm* — Foley & Lardner LLP

(57) ABSTRACT

An expandable implant assembly includes an upper endplate assembly, a lower endplate assembly, and a control assembly. The upper endplate assembly is configured to engage bone and includes an upper base member and a plurality of upper endplates. Each of the plurality of upper endplates is coupleable to the base member. The lower endplate assembly is configured to engage bone and includes a lower base member and a plurality of lower endplates. Each of the plurality of lower endplates is coupleable to the base member. The control assembly is configured to couple the upper endplate assembly to the lower endplate assembly and control movement of the upper endplate assembly relative to the lower endplate assembly.

18 Claims, 25 Drawing Sheets

(56) References Cited

U.S. PATENT DOCUMENTS

| | | | | |
|---|---|---|---|---|
| 11,173,044 | B1 * | 11/2021 | Jones | A61F 2/447 |
| 11,191,650 | B2 | 12/2021 | Weiman et al. | |
| 11,291,559 | B1 | 4/2022 | Yoon et al. | |
| 2013/0035763 | A1 | 2/2013 | Krueger | |
| 2018/0338838 | A1 | 11/2018 | Cryder et al. | |
| 2019/0110902 | A1 * | 4/2019 | Vigliotti | A61F 2/447 |
| 2019/0274838 | A1 | 9/2019 | Manwill et al. | |
| 2021/0093457 | A1 | 4/2021 | Hodrinsky et al. | |
| 2021/0093462 | A1 * | 4/2021 | Lucasiewicz | A61F 2/4455 |
| 2021/0386555 | A1 | 12/2021 | Hessler et al. | |
| 2022/0008204 | A1 | 1/2022 | Su et al. | |
| 2022/0104951 | A1 | 4/2022 | Predick et al. | |
| 2022/0183854 | A1 * | 6/2022 | Altarac | A61F 2/4611 |
| 2022/0313449 | A1 | 10/2022 | Besaw et al. | |
| 2022/0370207 | A1 | 11/2022 | Hessler et al. | |

* cited by examiner 20
24

20
24

46
20
44
24

EXPANDABLE IMPLANT ASSEMBLY WITH MODULAR ENDPLATES

CROSS-REFERENCE TO RELATED PATENT APPLICATIONS

This U.S. non-provisional patent application claims the benefit of and/or priority under 35 § U.S.C. 119(e) to U.S. provisional patent application Ser. No. 63/496,537 filed Apr. 17, 2023 titled "Expandable Implant Assembly with Modular Endplates," the entire contents of which is specifically incorporated herein by reference.

BACKGROUND

The present disclosure relates to spinal interbody and intravertebral body devices and, more particularly, to vertebral interbody and intravertebral devices that are expandable after spinal placement thereof and are capable of providing varying heights and/or degrees of angulation Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posterolaterally.

Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

SUMMARY

One embodiment relates to an expandable implant assembly, including an upper endplate assembly configured to engage bone, the upper endplate assembly including an upper base member; a plurality of upper endplates, wherein each of the plurality of upper endplates is coupleable to the base member; a lower endplate assembly configured to engage bone, the lower endplate assembly including a lower base member; a plurality of lower endplates, wherein each of the plurality of lower endplates is coupleable to the base member; and a control assembly configured to couple the upper endplate assembly to the lower endplate assembly and control movement of the upper endplate assembly relative to the lower endplate assembly Another embodiment relates to a method of configuring an implant, including selecting an upper endplate from a plurality of upper endplates; selecting a lower endplate from a plurality of lower endplates; coupling the upper endplate to an upper base member and coupling the lower endplate to a lower base member to form an implant, the implant including an upper endplate assembly including the upper endplate and the upper base member; a lower endplate assembly including the lower endplate and the lower base member; and a control assembly operatively coupling the upper plate assembly to the lower plate assembly and configured to control relative movement between the upper endplate assembly and the lower endplate assembly.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION

Figure 1:
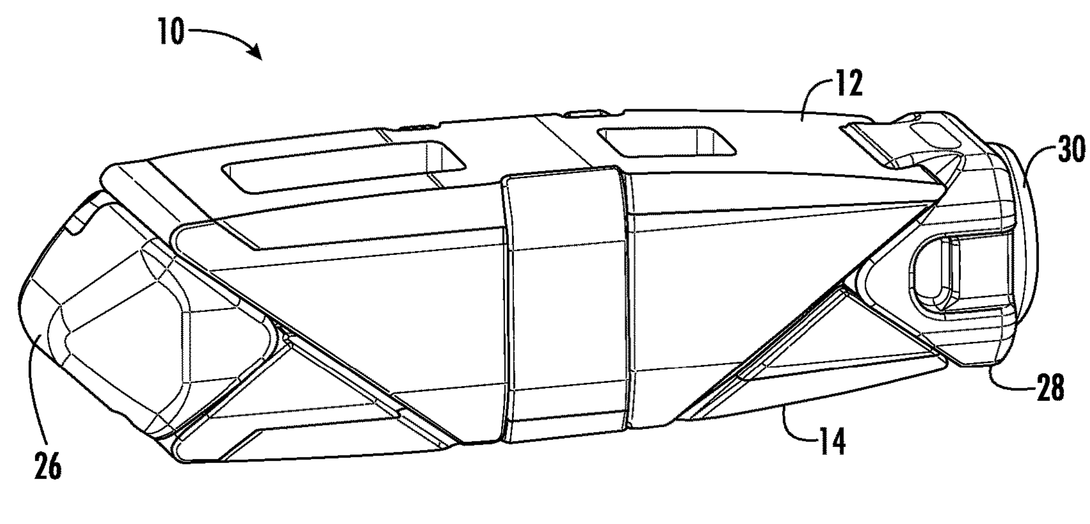
FIG. 1 is a perspective view of an implant in a collapsed position according to an example embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

The present disclosure relates to expandable and/or dynamic interbody (between adjacent vertebrae), intravertebral-body (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization, and/or promoting bone growth between or inside vertebrae that have been destabilized or otherwise impaired due to injury, illness and/or the like. Particularly, the present disclosure provides various embodiments of dynamic (expandable and/or expandable and retractable) interbody/intravertebral body devices that are usable in a spinal column of a human.

Various embodiments disclosed herein are directed to expandable implant assemblies including modular endplate assemblies. An implant assembly may have upper and lower endplate assemblies. Each endplate assembly may include a base member and an endplate. The endplates may be selected from a plurality of endplates that provide different characteristics (e.g. different heights, widths, constructions, materials, degrees of angulation, protrusions, graft windows, etc., or combinations thereof) for the implant assembly. As such, by selecting appropriate endplates for a particular type of application, the size and fit of the implant assembly may be customized without needing numerous different implant assemblies to accommodate all of the different size/fit combinations. An assembly, or kit, with multiple endplates that may be selectively coupled to the base members may be used to address a variety of different situations.

Referring to FIGS. 1-4, an expandable implant assembly 10 is shown according to one embodiment. The implant 10 is configured to be implanted or inserted into a human spine or other area of the human anatomy. The implant 10 may be implanted between adjacent upper and lower vertebrae of the spine (e.g., interbody or intervertebral).

According to various embodiments and as discussed in greater detail below, the components of implant 10 may be made of any suitable material(s), including a variety of metals, plastics, composites, or other suitable bio-compatible materials. In some embodiments, one or more components of implant 10 may be made of the same material, while in other embodiments, different materials may be used for different components of implant 10.

Implant 10 is usable, for example, between and/or within vertebral bodies of the spine. It should be understood that implant 10 may in some embodiments be usable in other portions of the body in addition to the spine, and all such applications are to be understood to be within the scope of the present disclosure.

According to one embodiment, implant 10 includes an upper endplate assembly 12 (e.g., a first or top support member or assembly) coupled to a lower endplate assembly 14 (e.g., a second or bottom support member or assembly) by way of a control assembly 16. Implant 10 is moveable between a collapsed position and an expanded position by manipulation of the control assembly 16 to vary a height of the implant 10.

In some embodiments, the upper endplate assembly 12 includes an upper base member 18 and an upper endplate 20. Similarly, the lower endplate assembly 14 includes a lower base member 22 and a lower endplate 24. The upper endplate 20 may be one of a number of upper endplates provided as part of implant 10. Similarly, the lower endplate 24 may be one of a number of lower endplates provided as part of implant 10 In other words, implant 10 may be provided with multiple upper and/or lower endplates 20, 24, such that a user may select upper and lower endplates having a desired size, shape, and/or other characteristic for a particular application. The upper and lower endplates may be of the same type (i.e., similar size, shape, material, etc.) and/or of different types. The selected endplates 20, 24 are secured to the corresponding bases 18, 22 prior to use of the implant 10. It should be noted that while the present disclosure may largely discuss the upper endplate assembly 12, the features discussed herein are equally applicable to the lower endplate assembly 14. Furthermore, certain features of one endplate may be provided on other endplates (e.g., in the case of multiple upper and/or lower endplates being provided as part of a single implant assembly).

In some embodiments, the control assembly 16 includes a distal wedge 26 (e.g., a first or forward wedge or member), a proximal wedge 28 (e.g., a second or rearward wedge or member), and a control shaft 30 (e.g., a control screw, threaded shaft, etc.). The control shaft 30 may be retained in position by way of one or more retaining members 32 that extend through proximal wedge 28 and are received in a groove or similar feature in the control shaft 30. However, other control assemblies may be used according to various alternative embodiments. The distal and proximal wedges 26, 28 engage the upper and lower endplate assemblies 12, 14 to move the implant 10 between a first, collapsed position (see, e.g., FIG. 1), and a second, expanded position (see, e.g., FIG. 6). The control shaft 30 may include a head and a threaded portion. One or more channels 34 (e.g., fluid channels) may extend from the head to a side of the control shaft to enable delivery of bone graft material or other material to the interior of the implant 10. In some embodiments, the implant 10 uses a control assembly such as that shown in U.S. Publication No. 2020/0383798, published Dec. 10, 2020, which is incorporated herein by reference. In other embodiments, the implant 10 may expand using a mechanism such as that shown in U.S. Publication No. 2021/0259852, published Apr. 26, 2021, which is incorporated herein by reference. Other suitable control assemblies may be used according to other embodiments.

Figure 2:
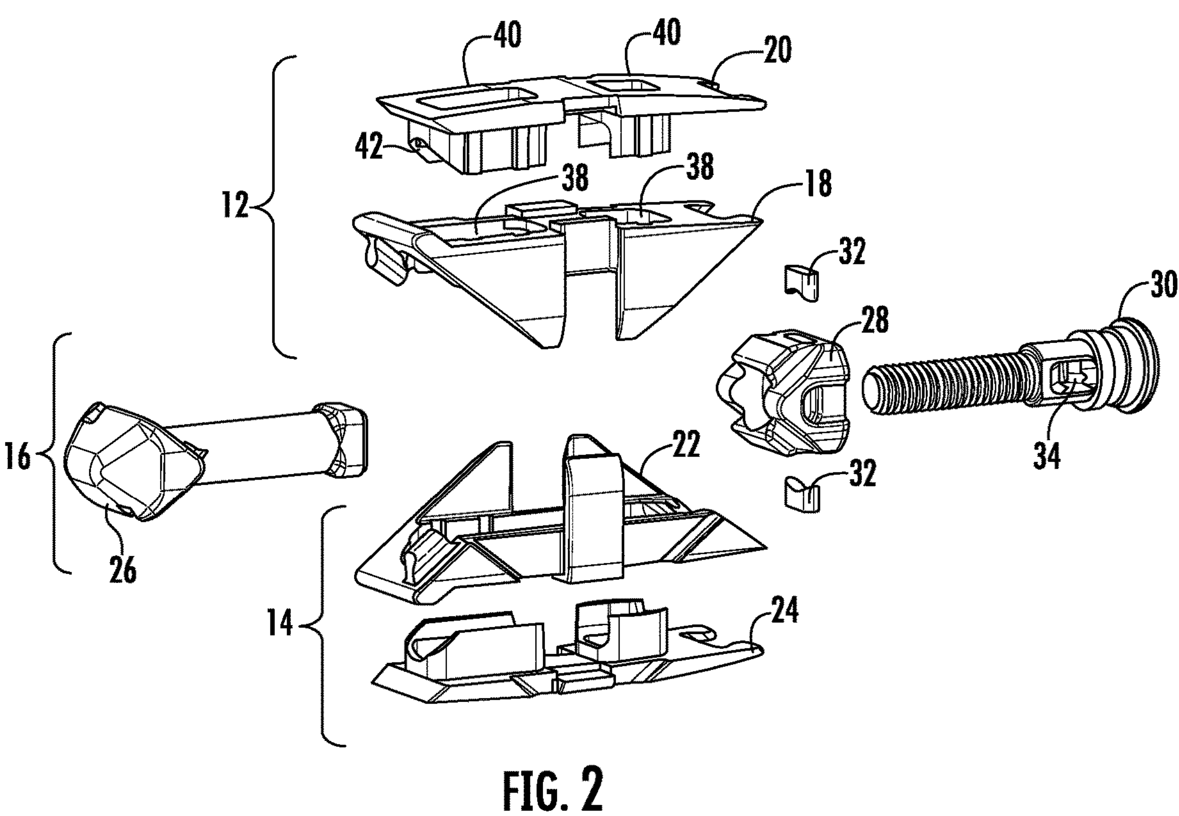
FIG. 2 is an exploded view of the implant of FIG. 1 according to an example embodiment.
Figure 3:
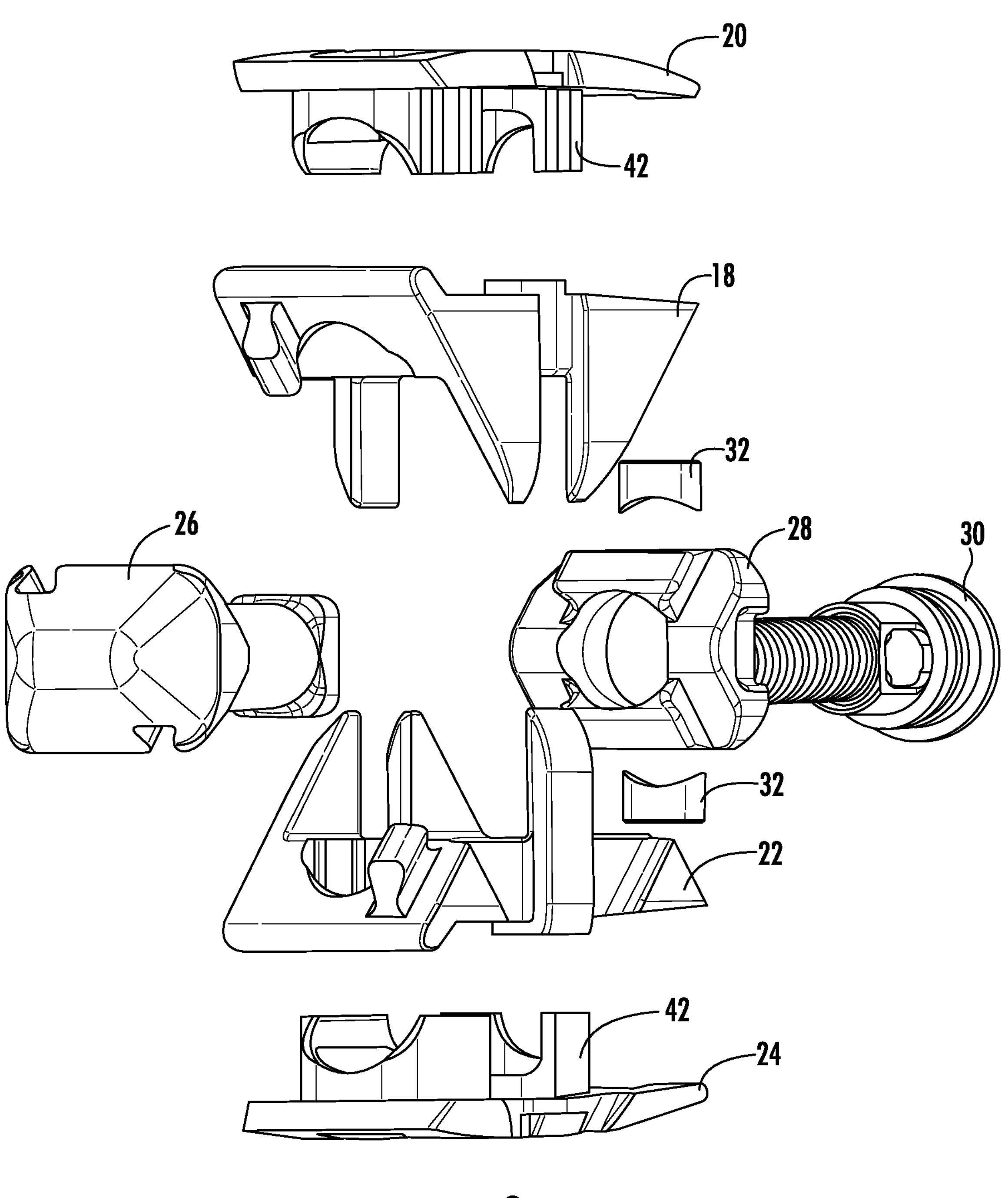
FIG. 3 is another exploded view of the implant of FIG. 1 according to an example embodiment.
Figure 4:
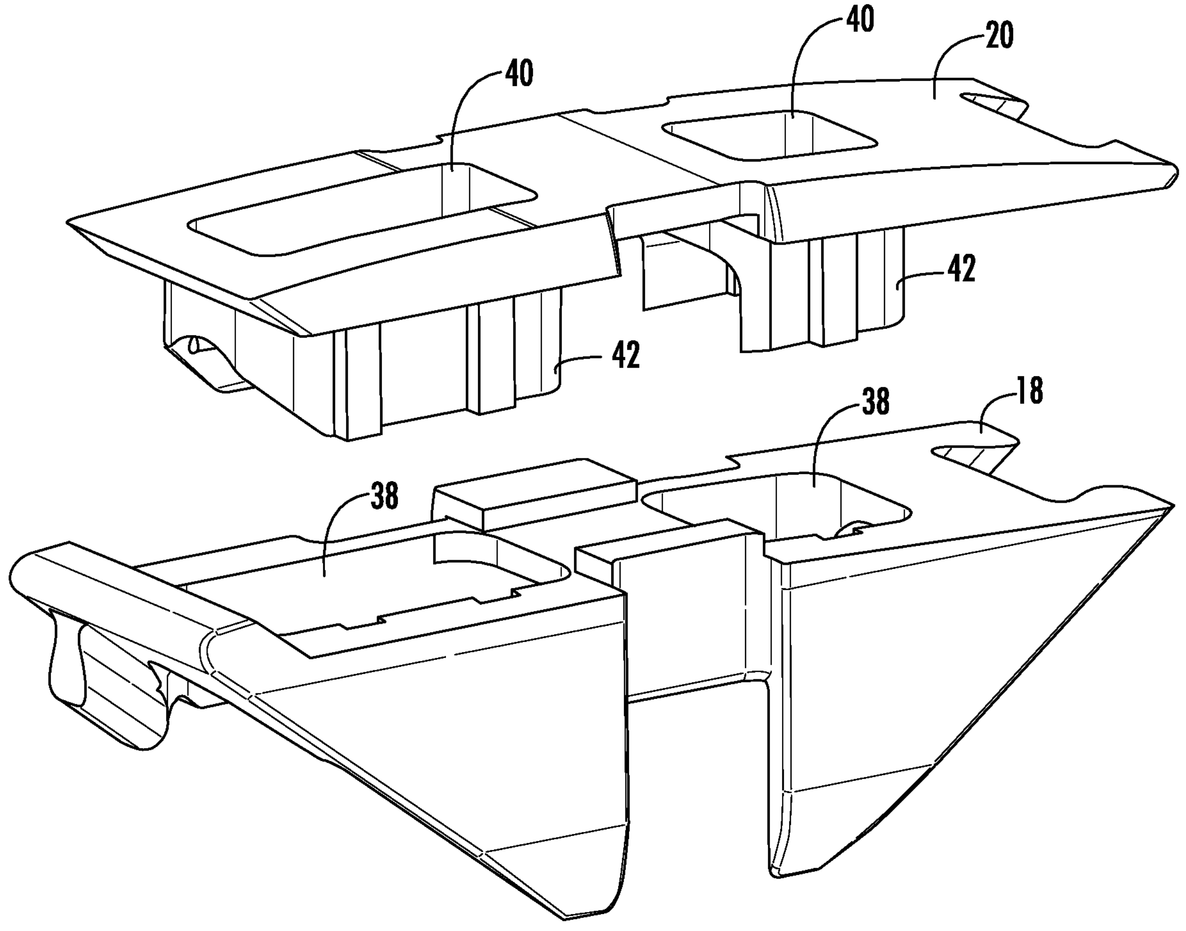
FIG. 4 is an exploded view of a base member and an endplate of the implant of FIG. 1 according to an example embodiment.

As shown in FIGS. 2-4, the upper endplate assembly 12 includes the upper base member 18 and an upper endplate 20 (e.g., selected from a number of possible endplates). The upper endplate 20 generally forms all or substantially all of the upper surface of the upper endplate assembly 12. In some embodiments, the upper base member 18 includes a lip 36 configured to provide a leading edge for the upper endplate assembly 12. Providing the lip 36 may decrease the chance of fracturing or otherwise breaking, damaging, etc., a portion of the upper endplate 20, for example, during insertion of implant 10 into a desired position. In some embodiments, the lip 36 may be made of a different material (e.g., steel, titanium) than the upper endplate 20, which may be made of a composite, polymer (e.g., polyether ether ketone (PEEK)), or other material.

In some embodiments, the upper and/or lower endplates 20, 24 may be injection molded to form a generally solid component. In other embodiments, the upper and/or lower endplates 20, 24 may be formed by additive manufacturing processes (e.g., 3D printing). In such embodiments, the endplates 20, 24 can be printed based on the specific application or anatomy of the patient. In some embodiments, the endplates 20, 24 can be printed before or during the operation/installation of the implant 10. In further embodiments, the upper and/or lower endplates 20, 24 may be in part of in whole of a porous structure (e.g., having voids throughout porous areas to promote ingrowth of bone, etc.).

In some embodiments, the upper base member 18 comprises at least one graft window 38 configured to enable ingrowth of bone into the interior of the implant 10. In some embodiments, the upper base member 18 includes first and second graft windows 38 that are longitudinally spaced apart along the length of the implant 10. In other embodiments, more or fewer graft windows 38 may be used, and the positioning of the graft windows 38 may vary from that shown in the Figures.

In some embodiments, the upper endplate 20 includes one or more graft windows 40 that are configured such that the graft windows 40 of the upper endplate 20 are generally aligned with the graft windows 38 of the upper base member 18 when the upper endplate 20 is secured to the upper base member 18. Furthermore, in some embodiments, the graft windows 40 on the upper endplate 20 are defined by columnar or similar structures or projections 42 that extend downward into the graft windows 38 on the upper base member 18. The projections 42 in some embodiments have an outer size and shape that at least in part corresponds to the interior size and shape of the graft windows 38 of the upper base member 18. The projections 42 are configured to facilitate securing the upper endplate 20 to the upper base member 18 and maintain proper alignment between the components. The projections 42 may include cut-outs, etc., to provide space for components of the control assembly 16 (control shaft 30, etc.). For example, as shown in FIG. 3, the projections 42 may be include an arc-shaped recess to provide space for and accommodate the control shaft 30 and/or other components.

In some embodiments, the upper endplate 20 and the upper base member 18 include corresponding securement features configured to provide a secure coupling of the upper endplate to the upper base member. For example, as described in further detail below with reference to FIGS. 21-43, the upper endplate 20 and the upper base member 18 may include press-fit portions, friction-fit components, deflecting tabs/recesses to provide a snap fit, and the like.

In various embodiments, implant 10 includes a number of upper endplates 20 and/or a number of lower endplates 24 (e.g., as a kit, etc.). Each upper endplate 20 can be selectively coupled to and/or decoupled from the upper base member 18, and each lower endplate 24 can be selectively coupled to and/or decoupled from the lower base member 22. As such, and as discussed in greater detail below, a user can select a desired upper endplate 20 and a desired lower endplate 24 to form part of implant 10. In some embodiments, the upper endplate 22 and/or the lower endplate 24 can be coupled to but not decoupled from the upper base member 18 and the lower base member 22, respectively. Each upper endplate 20 can be different from some of or the remainder of upper endplates 20 in height, width, angulation, material, construction, or in some other physical or functional characteristic. Similarly, each lower endplate 24 can be different from some of or the remainder of the lower endplates 24 in height, width, angulation, material, construction, or in some other physical or functional characteristic. Moreover, each upper endplate 20 can be different from some or all of the lower endplates 24 in height, width, angulation, material, construction, or in some other physical or functional characteristic.

Figures 5, 6:
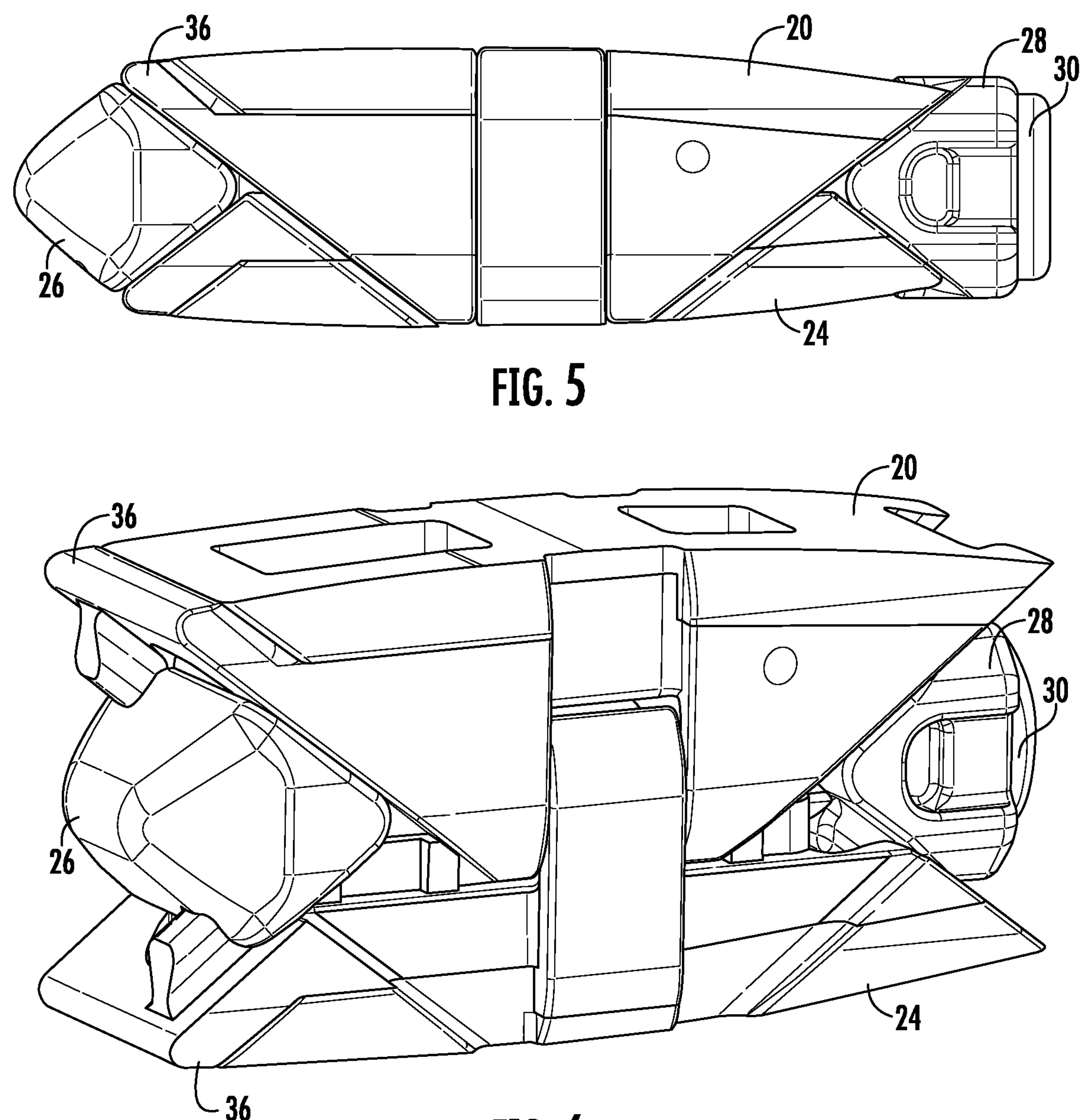
FIG. 5 is a right side view of the implant of FIG. 1 according to an example embodiment.
FIG. 6 is a perspective view of the implant of FIG. 1 in an expanded position according to an example embodiment.
Figure 7:
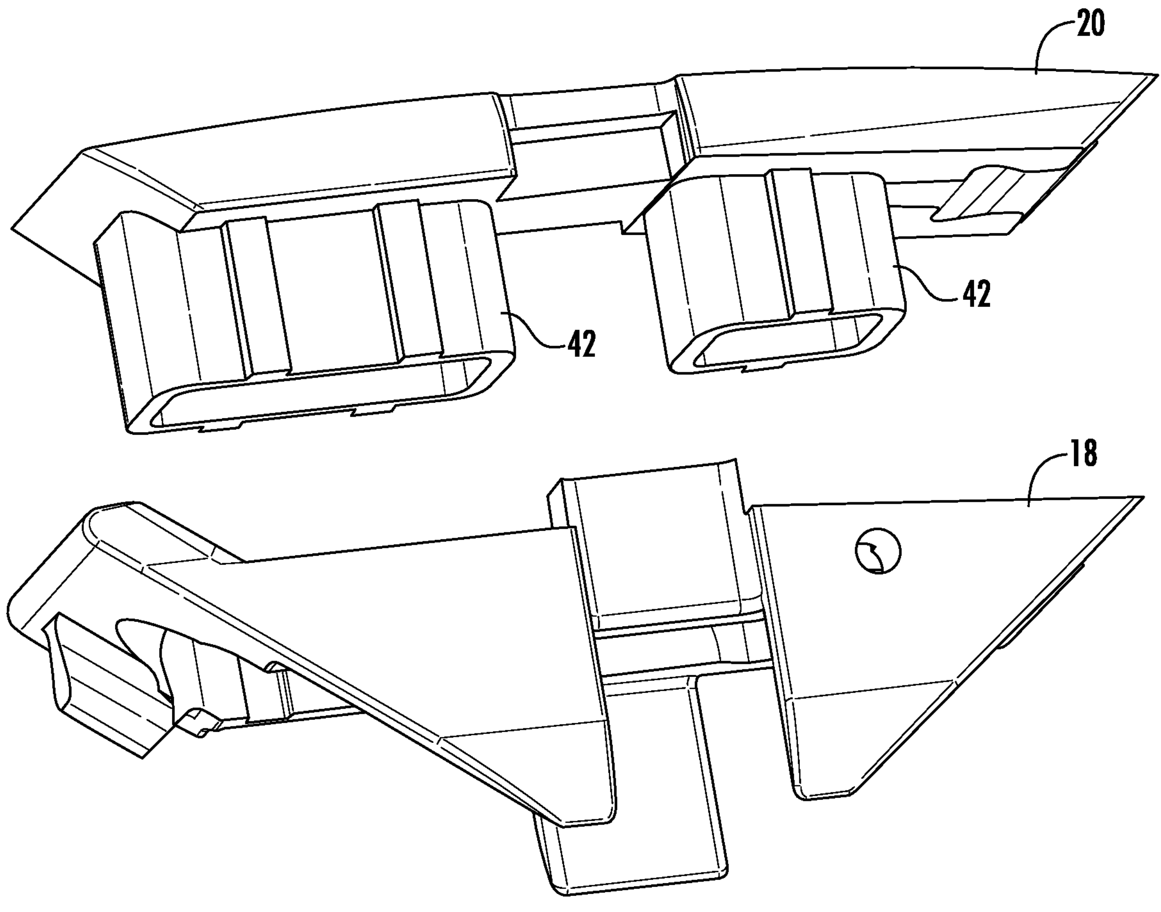
FIG. 7 is another exploded view of a base member and an endplate of the implant of FIG. 1 according to an example embodiment.

For example, referring to FIGS. 5-7, implant 10 is shown as having an upper endplate 20 with a greater height than the height of the upper endplate 20 shown in FIGS. 1-4. Similarly, the lower endplate 24 shown in FIGS. 5-7 has a greater height than the height of the lower endplate 24 shown in FIGS. 1-4. A single implant 10 may be provided with both higher/taller and lower/shorter endplates (e.g., as a kit). As such, a user can select any combination of upper endplates 20 and lower endplates 24 to use as part of implant 10. For example, should a user desire a lower profile implant, the user can select the relatively lower/shorter top and bottom end plates 20, 24. Conversely, should the user desire a higher profile implant, the user may select the higher/taller top and bottom endplates 20, 24. Similar to height, one or more endplates 20, 24 may vary in width, shape, material, or other physical or functional characteristic providing various options to a user in terms of widths or other characteristics of top and/or bottom endplates 20, 24.

In some embodiments, implant 10 may be provided with upper endplates 20 and/or lower endplates 24 having varying angulation. For example, it may be desirable for implant 10 to accommodate different curvatures of the spine. To do so, the top and/or bottom endplates 20, 24 may include an angled surface or surfaces (e.g., such that the top and bottom surfaces of the endplate are not parallel on one or both ends). Angulated surfaces may be provided on the top and/or bottom endplates 20, 24, and may be provided on one or both ends of the endplates 20, 24.

Figure 17:
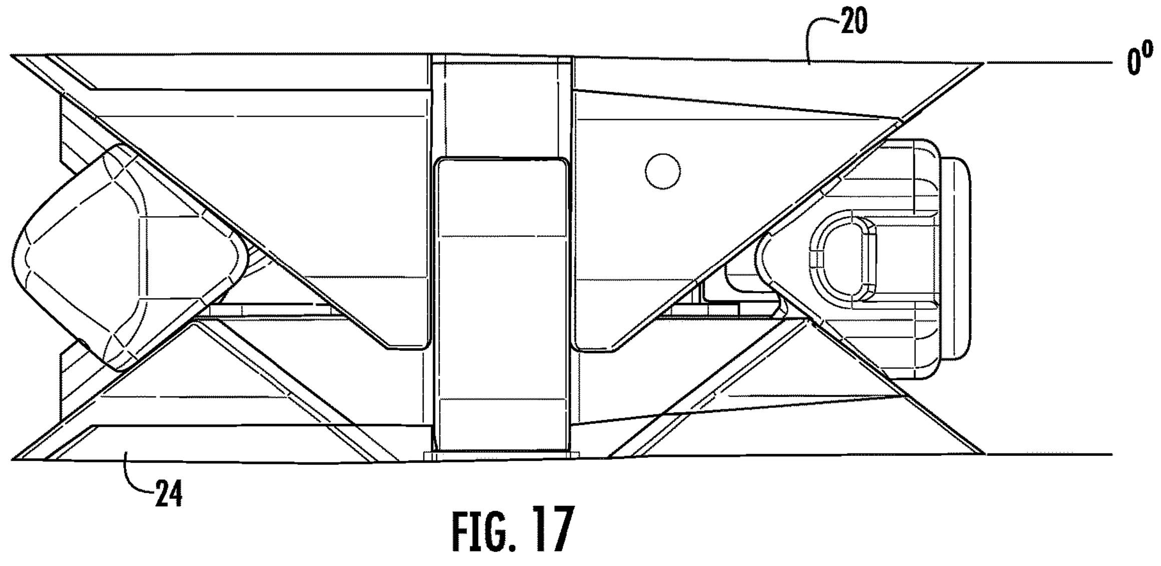
FIG. 17 is a right side view of the implant of FIG. 1 with endplates with no angulation according to an example embodiment.
Figure 18:
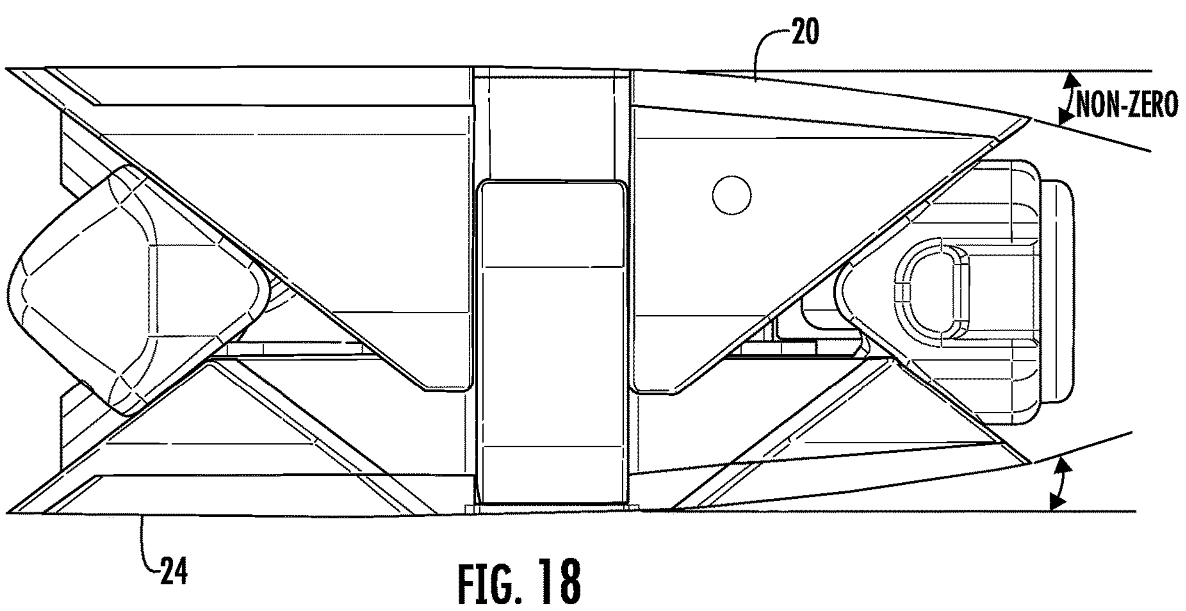
FIG. 18 is a right side view of the implant of FIG. 1 with endplates with non-zero angulation according to an example embodiment.
Figure 19:
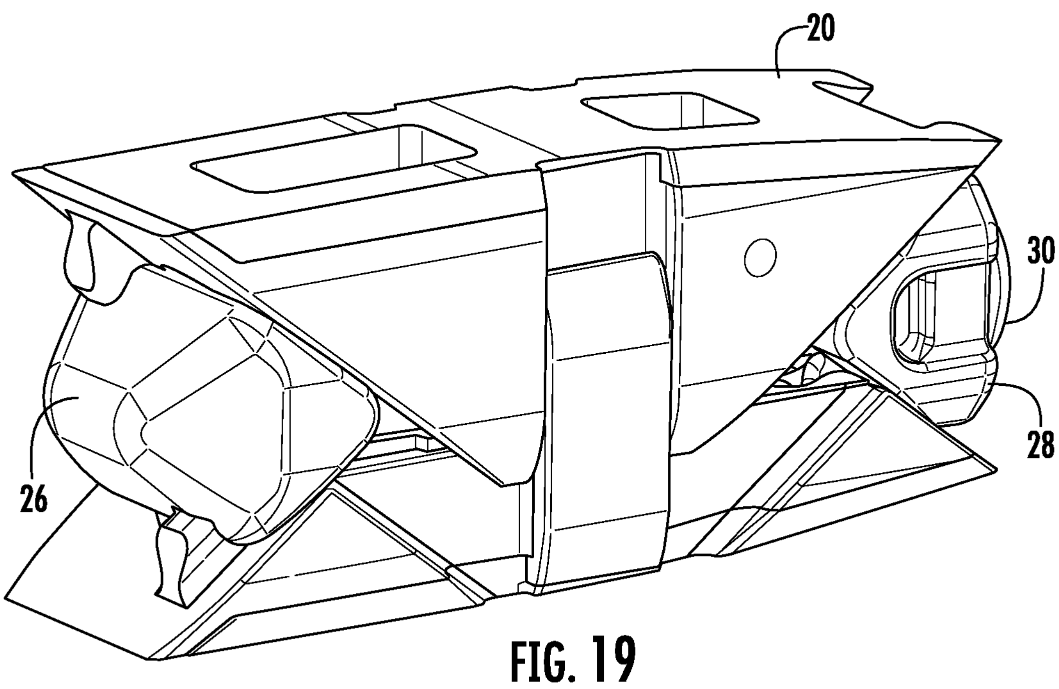
FIG. 19 is a perspective view of the implant of FIG. 1 according to an example embodiment.
Figure 20:
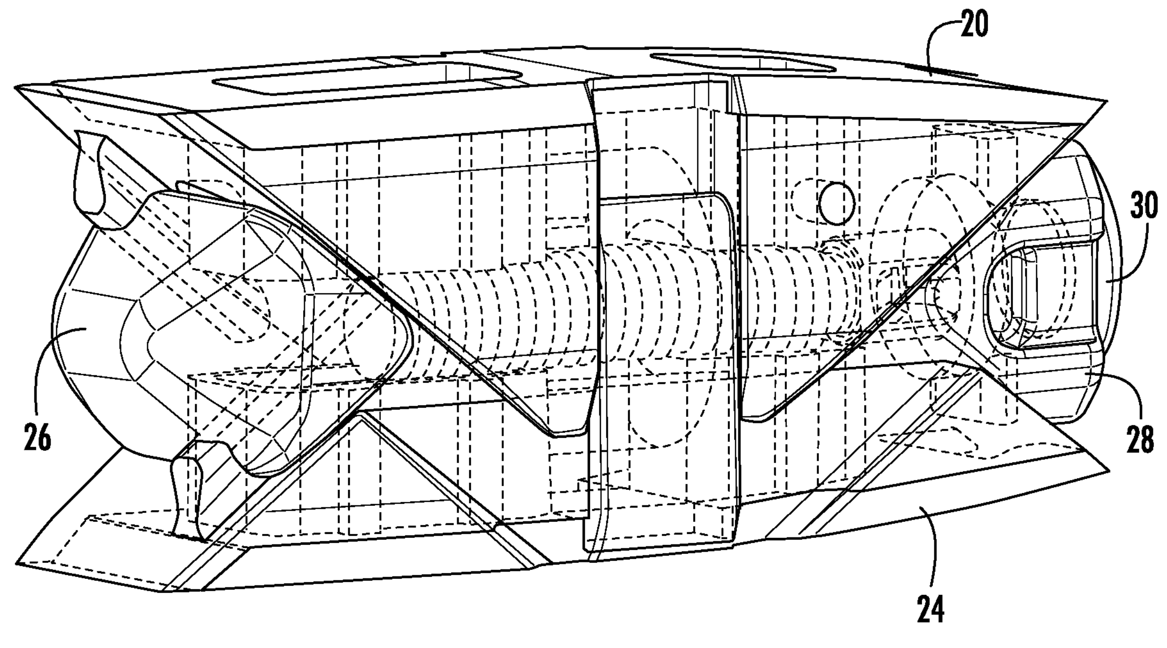
FIG. 20 is a perspective view of showing an internal arrangement of the implant of FIG. 1 according to an example embodiment.

For example, referring to FIGS. 17-18, implant 10 may be provided with top and bottom endplates 20, 24 with no (0 degrees angulation), as shown in FIG. 17, or may be provided with top and/or bottom endplates 20, 24 having non-zero angulation (e.g., 5 degrees, 10 degrees, 15 degrees, etc.). Implant 10 may be provided with one or more endplates 20, 24 having different degrees of angulation at one or both ends.

In some embodiments, implant 10 may include endplates 20, 24 providing varying overall stiffnesses for the endplate assemblies 12, 14. For example, referring to FIGS. 8-12, implant 10 is shown as including a top endplate 20 and bottom endplate 24 with a material having a different modulus of elasticity and/or structural features that modify the overall “stiffness” of the endplate assemblies 12, 14. For example, while some of the endplates disclosed herein may be made of stainless steel, the endplates shown in FIGS. 8-12 may be made of PEEK or another material or combination of materials having a different modulus of elasticity (e.g., to more closely replicate the elasticity of bone, etc.).

Figures 8, 9, 10:
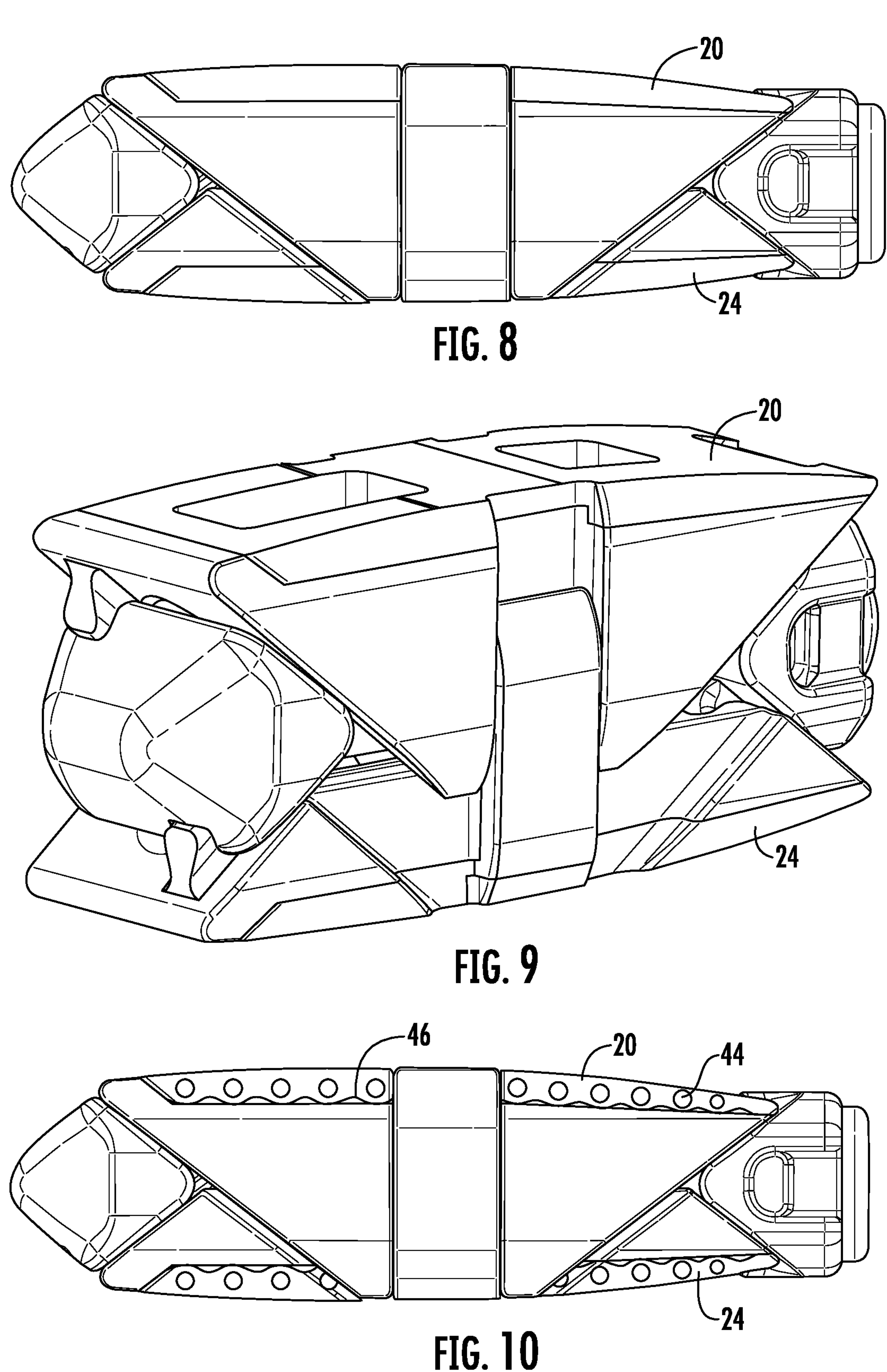
FIG. 8 is another right side view of the implant of FIG. 1 according to an example embodiment.
FIG. 9 is another perspective view of the implant of FIG. 2 in an expanded position according to an example embodiment.
FIG. 10 is a right side view of the implant of FIG. 1 in a collapsed position with a plurality of apertures in an upper endplate and lower endplate according to an example embodiment.
Figure 11:
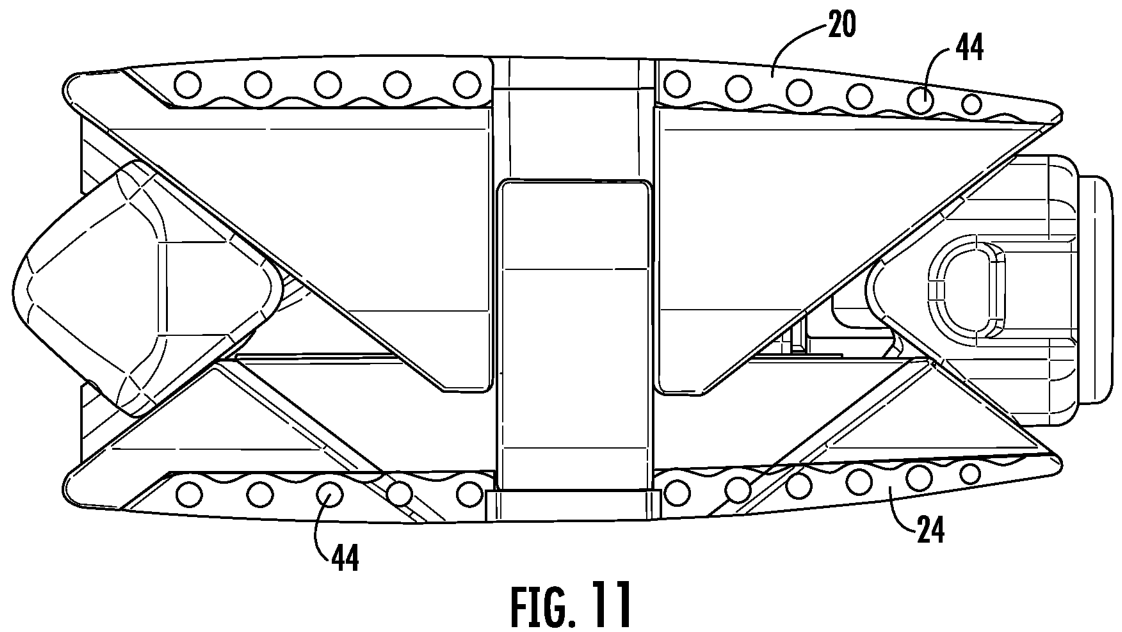
FIG. 11 is a right side view of the implant of FIG. 10 in an expanded position according to an example embodiment.
Figure 12:
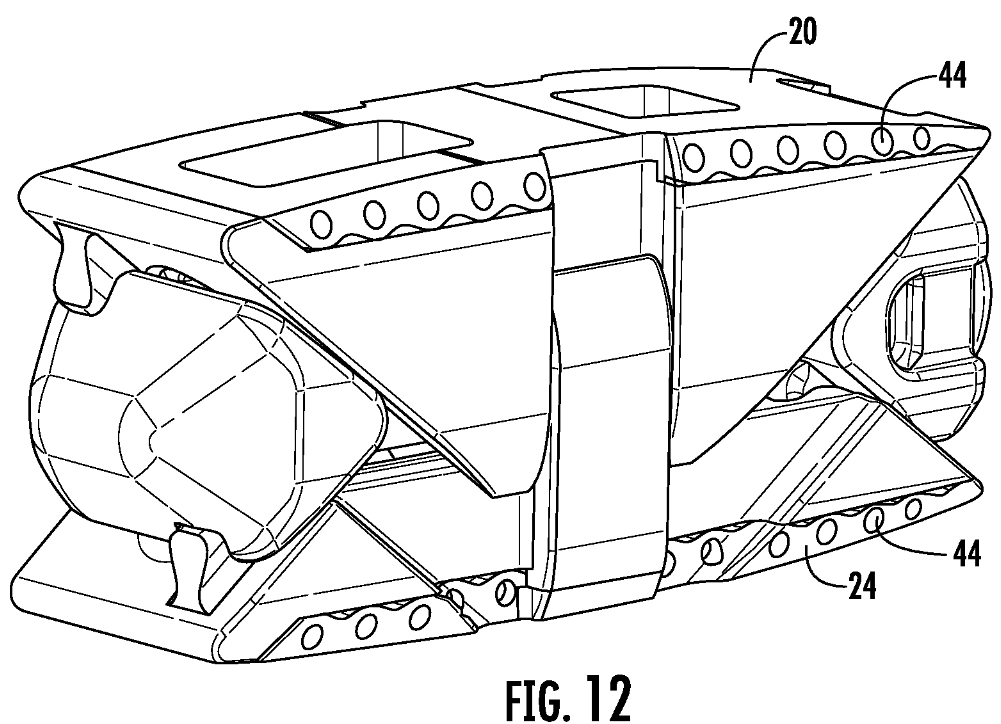
FIG. 12 is a perspective view of the implant of FIG. 10 in an expanded position according to an example embodiment.
Figure 13:
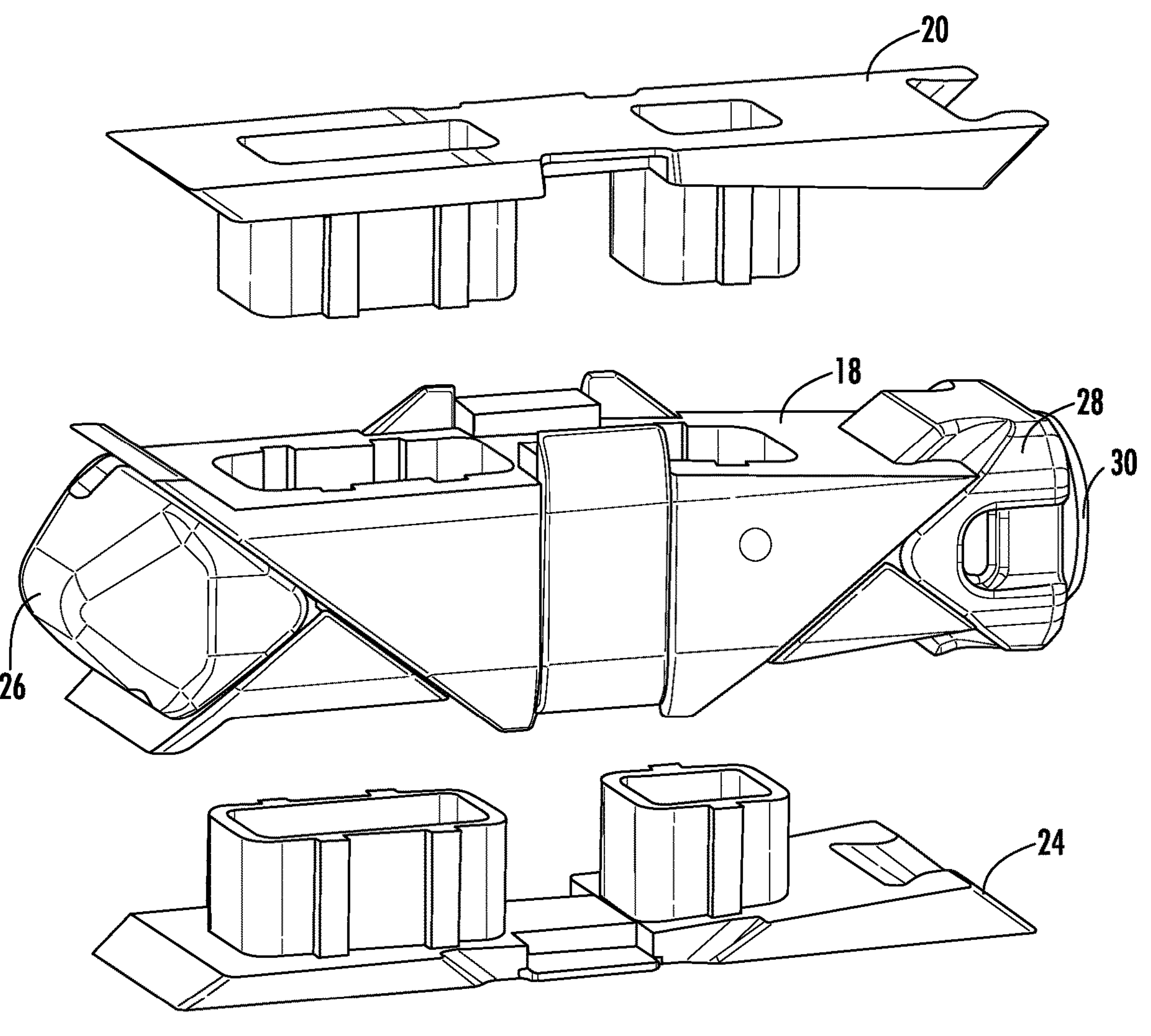
FIG. 13 is a partially exploded view of the implant of FIG. 1 with an upper and lower endplate with projections according to an example embodiment.
Figures 14, 15:
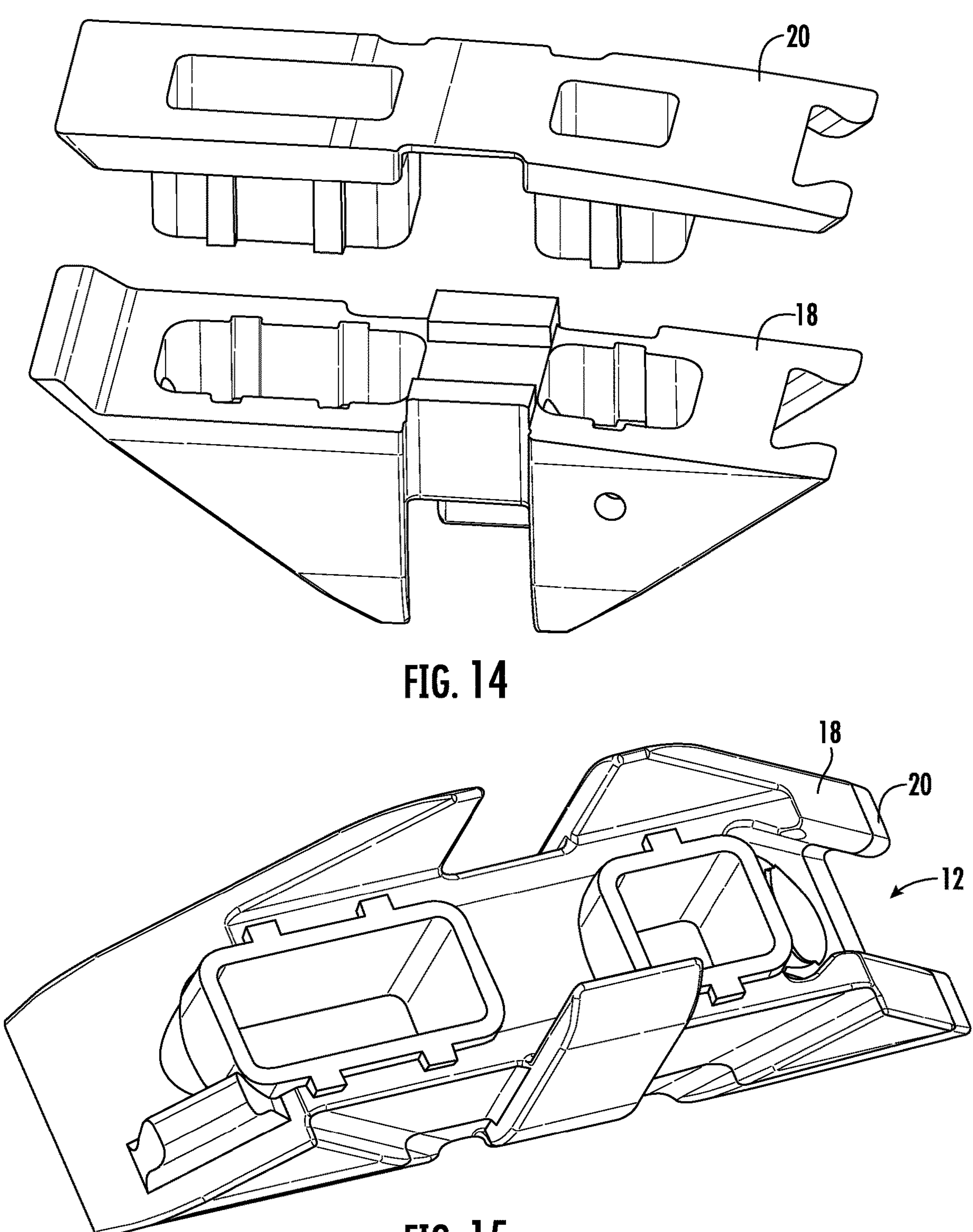
FIG. 14 is an exploded view of the implant of FIG. 13 with a base member and an endplate with projections according to an example embodiment.
FIG. 15 is a perspective view of an underside of an upper base member of the implant of FIG. 13 according to an example embodiment.
Figure 16:
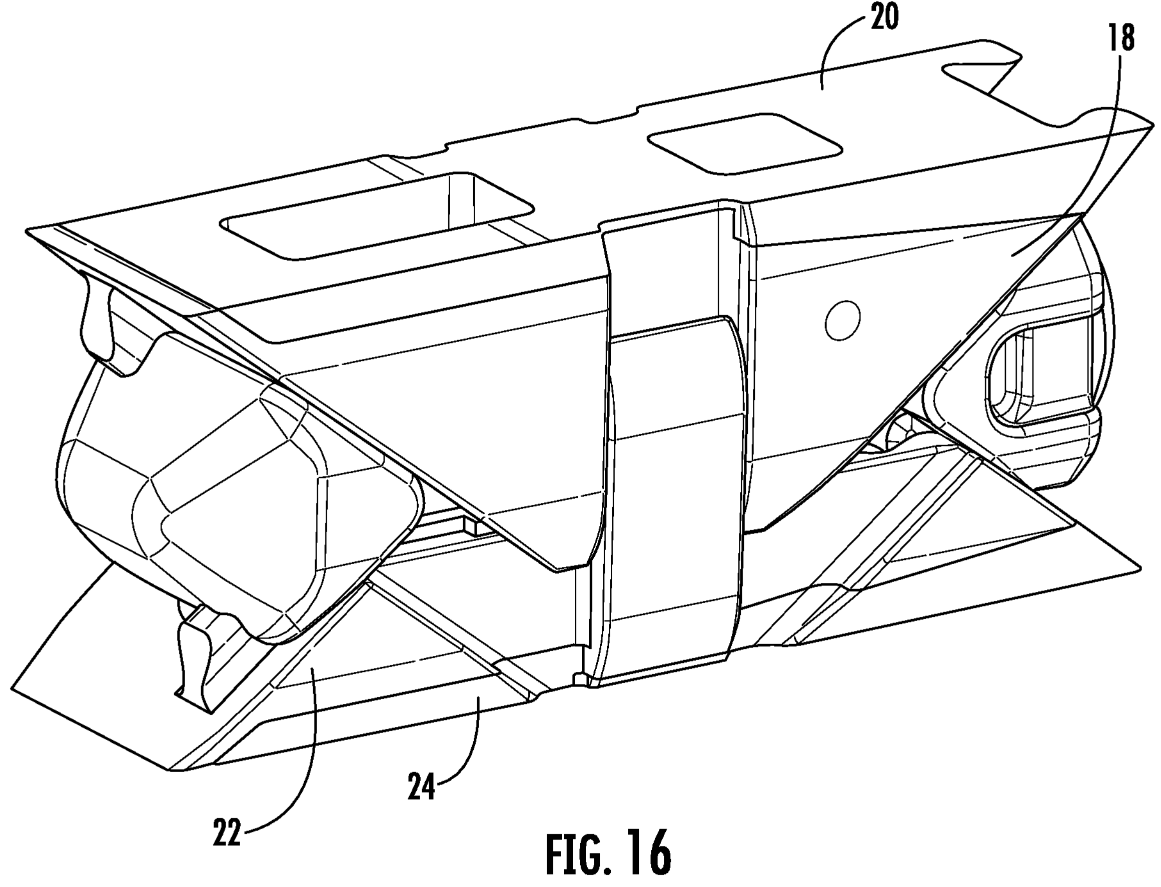
FIG. 16 is perspective view of the implant of FIG. 13 in an expanded position according to an example embodiment.

Furthermore, as shown in FIGS. 10-12, the top and bottom endplates 20, 24 are shown to have structural features that provide a more resilient endplate assembly 12, 14 relative to a completely solid endplate made of a more rigid material. For example, the top endplate 20 may include apertures 44 (e.g., through or stopped bores extending laterally through the top endplate). The apertures 44 may enable the top endplate 20 to be compressed more easily relative to a solid component, thereby reducing the overall stiffness of the component. The apertures 44 may extend along the side of the endplate 20 and may be longitudinally spaced apart from one another. The apertures 44 may extend fully through from one side to another side of the endplate 20. Alternatively, the apertures 44 may extend from both sides of the endplate 20 and only partially through (e.g., as a stopped bore).

Further, the top endplate 20 may have an uneven lower surface 46 that provides gaps or an otherwise uneven interface between the lower surface 46 of the top endplate 20 and the upper surface of the top base member 18. The gaps may be configured to enable compression of the top endplate 20 relative to the top base member 18, thereby decreasing the overall stiffness of the top endplate assembly 12. For example, FIGS. 10-12 illustrate the inner surface 44 of the top endplate 20 having a waved surface. In other embodiments, other configurations may be used (e.g., straight-lined, irregular undulations, regular undulations, etc.). The surface geometry may be configured such that the gaps extend from one side of the top endplate 20 to a second side of the top endplate 20. The surface geometry may further extend along all or part of a length and/or width of the inner surface 44 of the top endplate 20.

Figure 31:
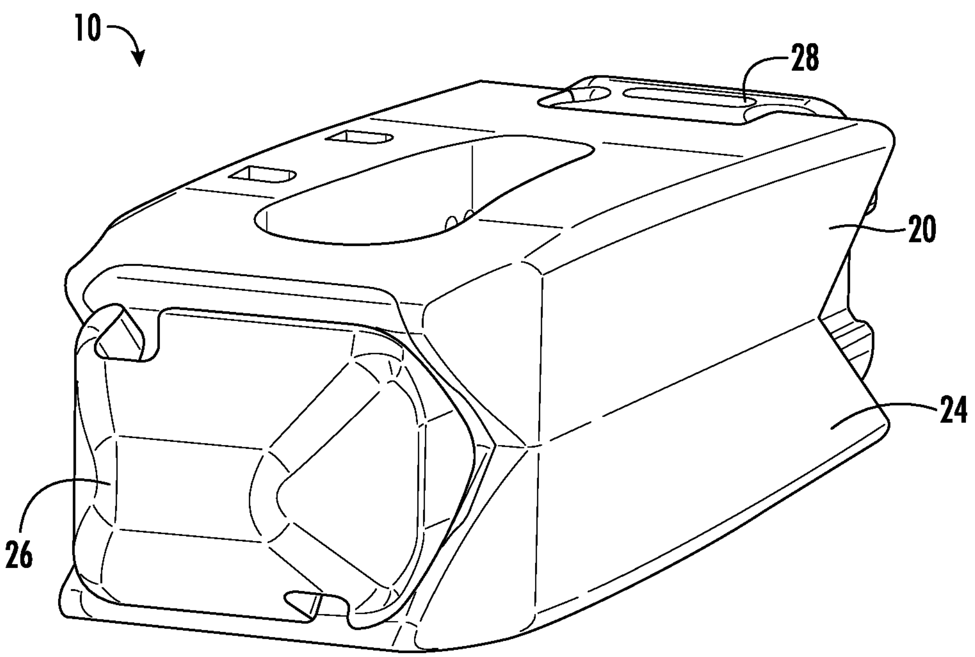
FIG. 31 is a perspective view of the implant of FIG. 1 with extended upper and lower endplates according to an example embodiment.
Figure 32:
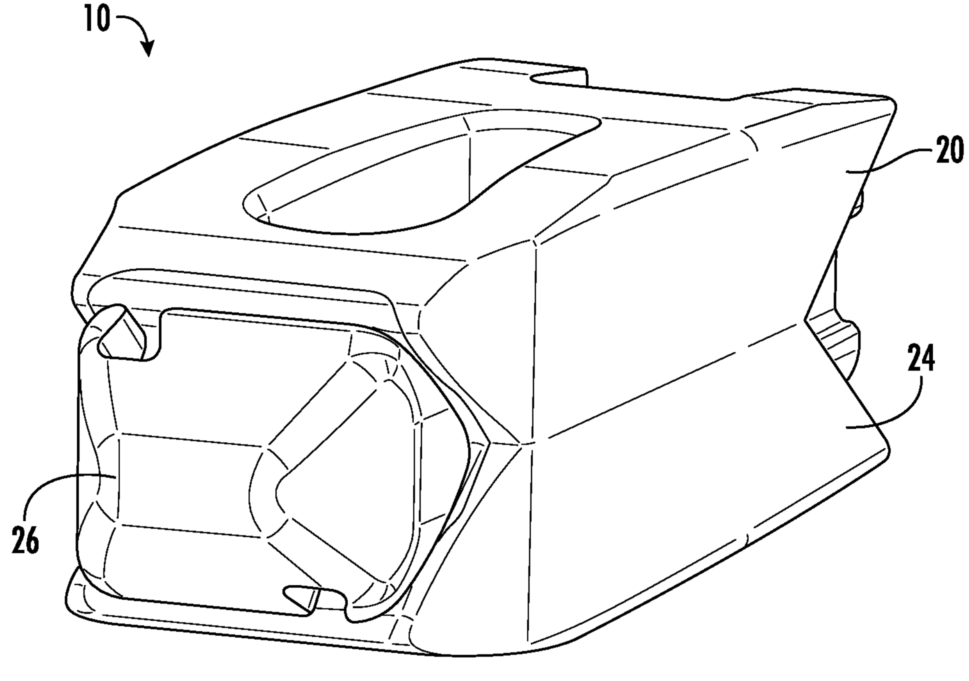
FIG. 32 is another perspective view of the implant of FIG. 1 with extended upper and lower endplates according to an example embodiment.
Figure 33:
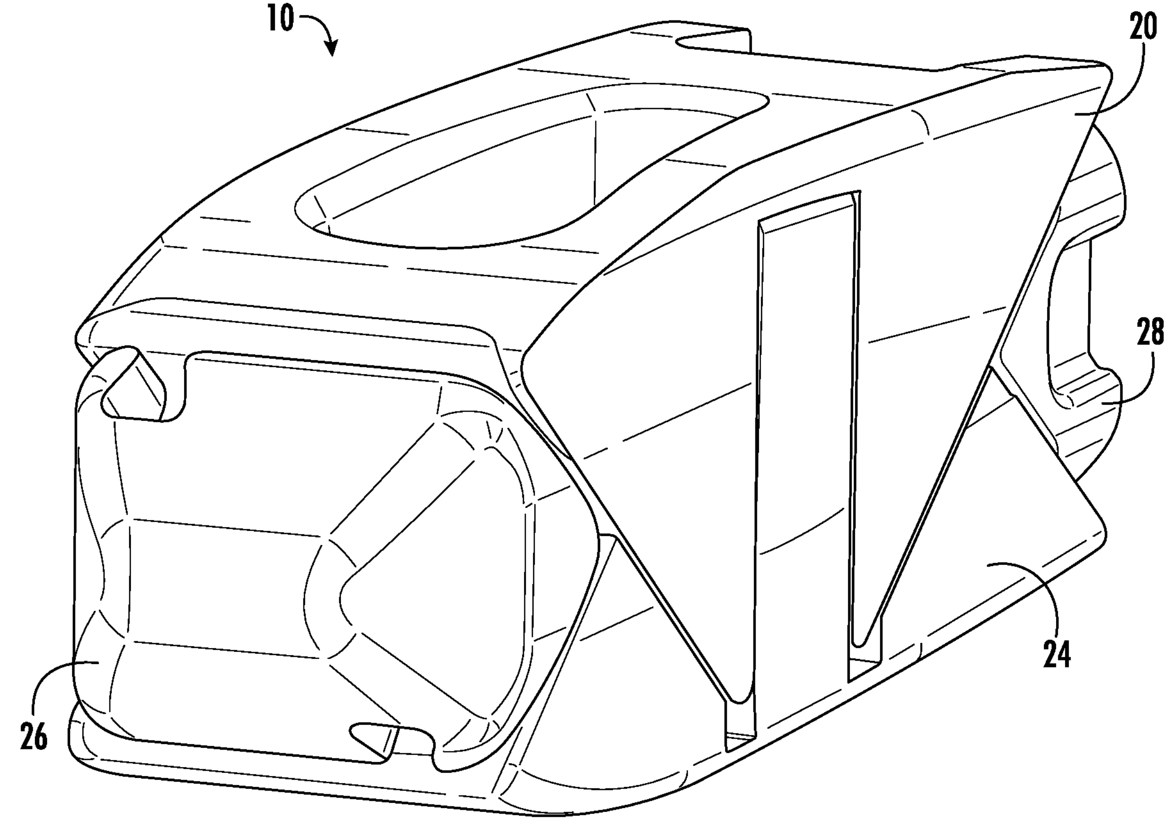
FIG. 33 is another perspective view of the implant of FIG. 1 with extended upper and lower endplates according to an example embodiment.
Figure 34:
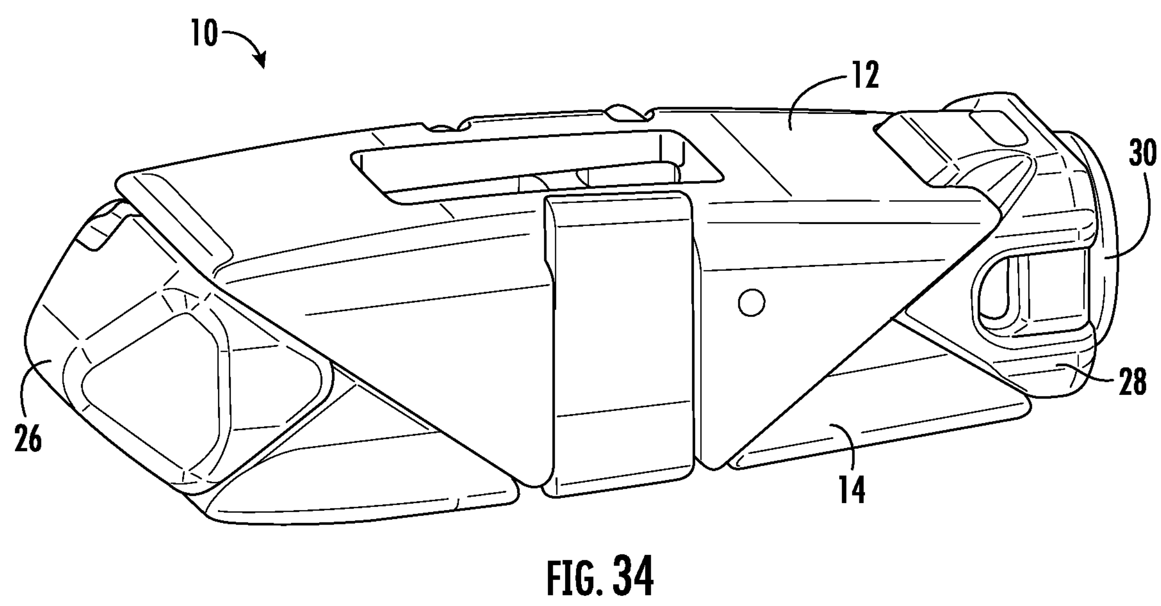
FIG. 34 is a perspective view of the endplate of FIG. 1 with locking upper and lower endplates in a collapsed position according to an example embodiment.

In some embodiments, implant 10 may include endplates 20, 24 having walls or skirts that extend and/or around the base members 18, 22 as shown in FIGS. 31-33. The skirts of the endplates 20, 24 may extend down such that in the collapsed position shown in FIGS. 31-33 the end plate 20 contacts or abuts the endplate 22. In some embodiments, the endplates 20, 24 include corresponding wedges or grooves. For example, as shown in FIG. 33 the skirts of the endplates 20, 24 interlock around the control assembly 16 and the base members 18, 22.

It should be noted that various different endplates may be provided with an alternate material, alternate structural features (e.g., apertures, uneven surfaces, etc.) or combinations thereof, to suit a particular application. Reducing the stiffness of one or both of the top and bottom endplate assemblies 12, 14 may reduce the likelihood of subsidence within the vertebral bodies and/or more closely mimic the modulus of elasticity of bone to improve conditions for fusion.

In some embodiments, an implant kit includes an implant 10 and a number of additional endplates 20, 24 that may be selectively coupled to top or bottom base members 18, 22 to provide an implant 10 having desired custom characteristics for a particular application. The endplates 20, 24 may provide the user with different heights, widths, degrees of angulation, material types, structural features (e.g., apertures, surface contours, etc.), and the like.

As noted above, implant 10 may utilize any appropriate components or mechanisms to expand the upper and lower endplate assemblies 12, 14. In some embodiments, the distal wedge 26 includes a rounded, or bull nose portion intended to facilitate insertion of implant 10 into a patient. The distal wedge 26 also includes ramped surfaces and grooves that facilitate controlled sliding movement between the distal wedge 26 and the upper and lower endplate assemblies 12, 14. Grooves on the ramped surfaces may be configured to receive projections on the upper and lower endplate assemblies 12, 14. Similarly, the proximal wedge 28 may include ramped surfaces and projections that are received within corresponding grooves on the upper and lower endplate assemblies 12, 14. It should be noted that the size, shape, and relative locations of the projections and grooves on the distal wedge 26, proximal wedge 28, and upper and lower endplate assemblies 12, 14 may be varied.

Figure 21:
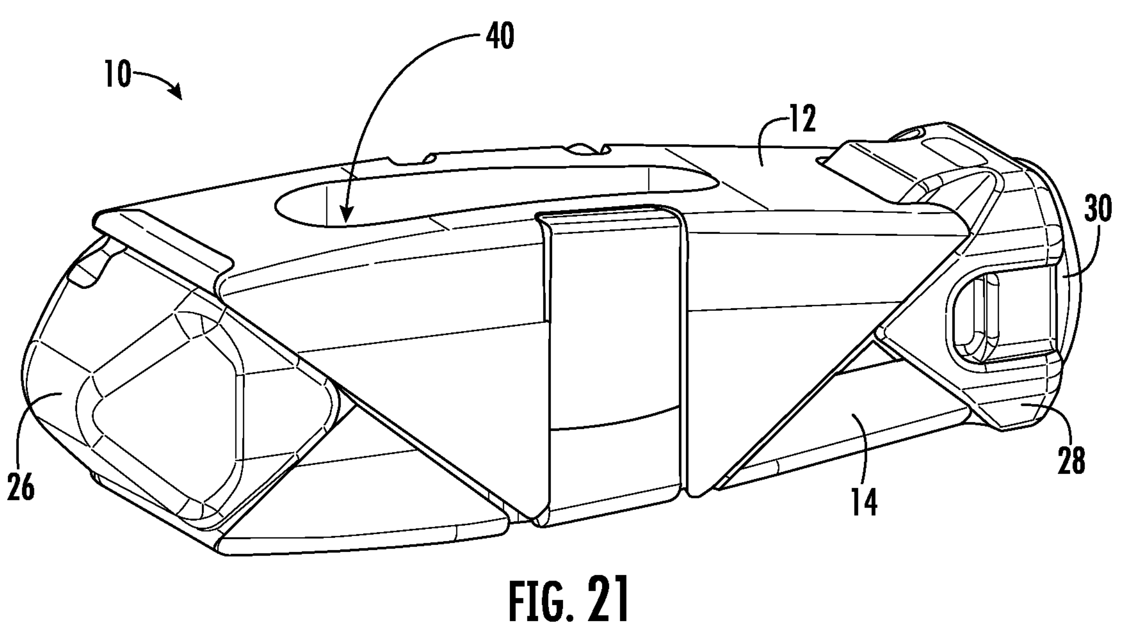
FIG. 21 is a perspective view of the implant of FIG. 1 with locking endplates in a collapsed position according to an example embodiment.
Figure 22:
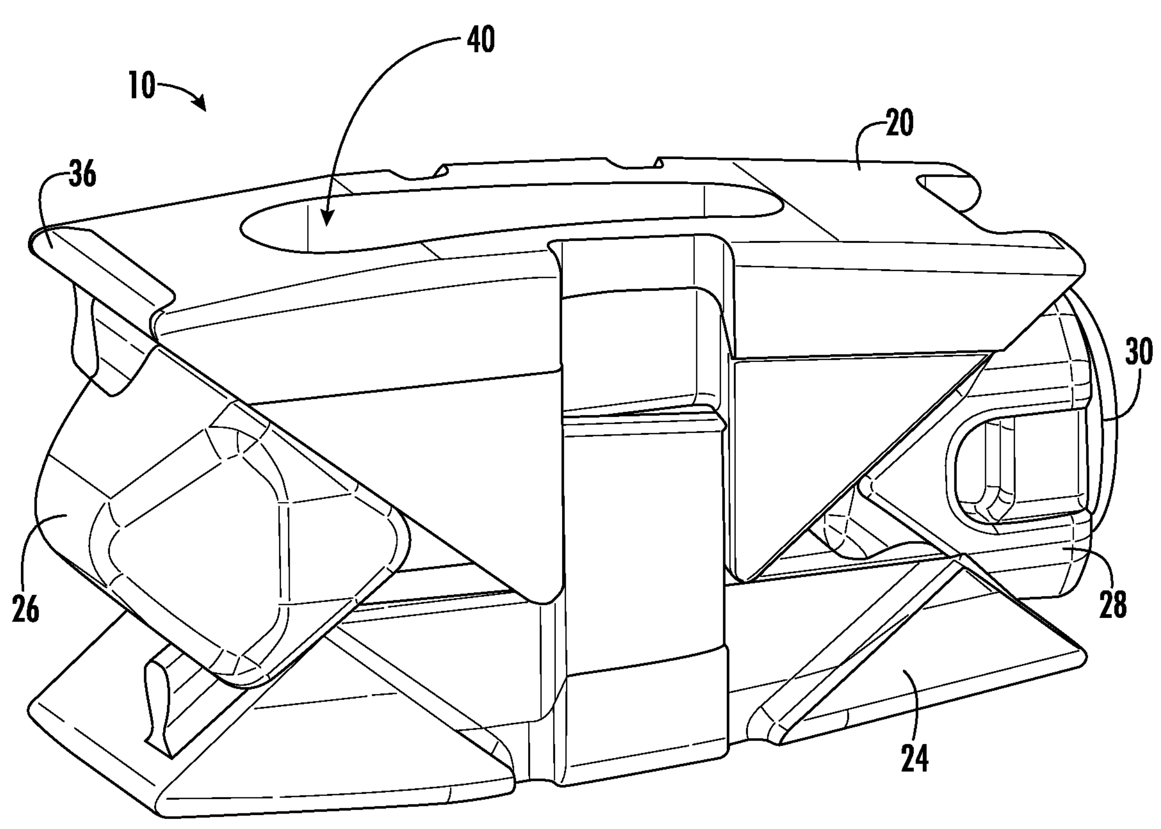
FIG. 22 is a perspective view of the implant of FIG. 21 in an expanded position according to an example embodiment.
Figure 23:
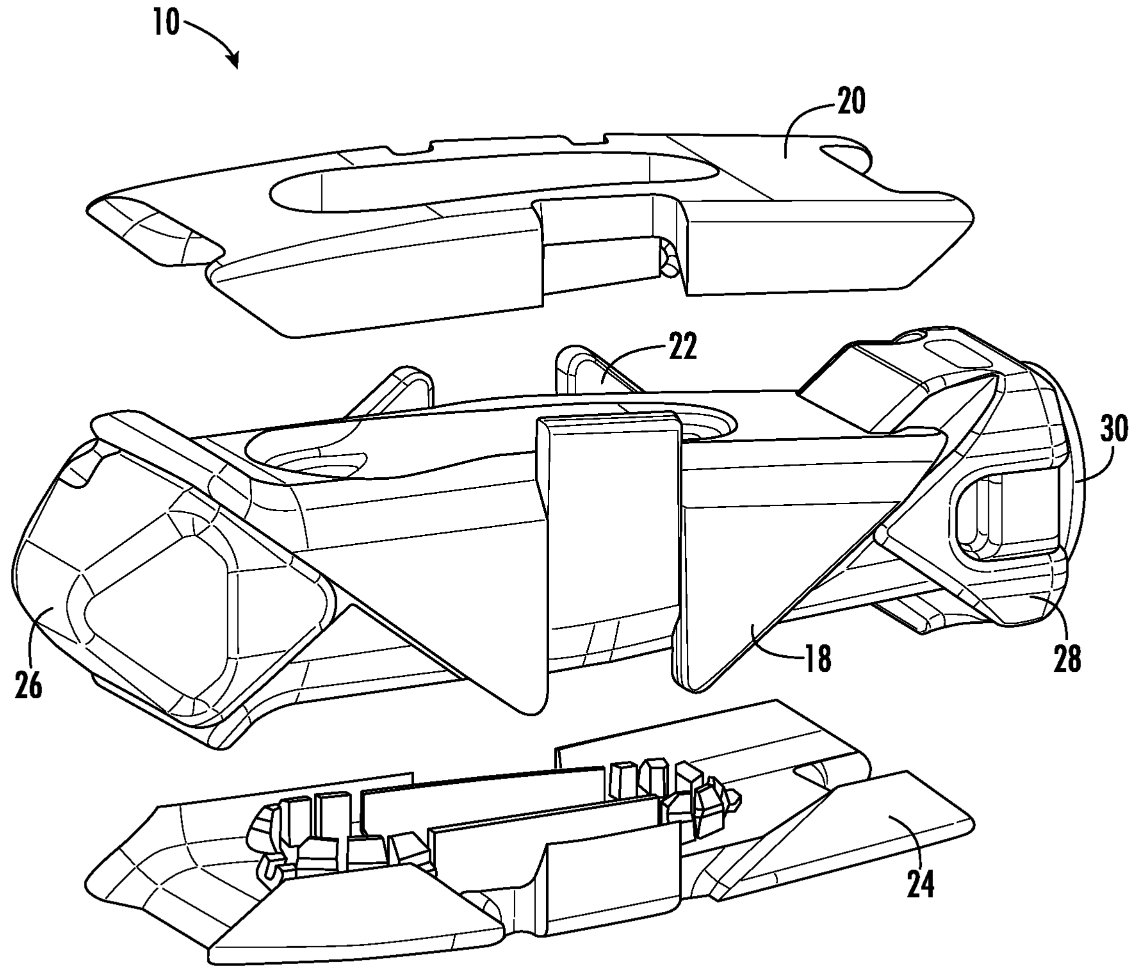
FIG. 23 is a partially exploded view of the implant of FIG. 21 according to an example embodiment.

As shown in FIGS. 21-23, the peripheral projections 40 (and the graft windows 40 defined thereby) of the endplates 20, 24 are asymmetric or otherwise irregularly shaped. In some embodiments, the graft windows 38 of the base members 18, 22 are also likewise asymmetric or otherwise irregularly shaped, and may also register, match or align with an interior wall (and the graft windows 40 defined thereby) of the endplates 20, 24. The asymmetric or otherwise irregular shaped properties of the projections 42 extending from the endplates 20, 24 and into the graft windows 38 of the base members 18, 22 are configured such that the endplates 20, 24 have only a single orientation in which they can be installed on the base members 18, 22.

A shown in FIGS. 24-27, the projections 42 extending away from the endplates 20, 24 and into the graft windows 38 of the base members 18, 22 act to provide a secure coupling of the endplates 20, 24 to the base member 18, 22. For example with reference specifically to FIGS. 24 and 25, the projections 42 include one or more cantilevered tabs or segments shown as teeth 48 separated by gaps 54 (e.g., slots, reliefs, etc.). In some embodiments, the projection 42 is composed of an elastically flexible material such that the teeth 48 deflect inward when passing through the graft window 38 of the base members 18, 22. The teeth 48 include a cantilever beam 50 extending away from the end plate 20, 24 that ends in a hook 52. The hook 52 extends outward away from a center of the graft window 40. In some embodiments, the hook 52 includes an angled, ramped, or sloped tip that acts as a wedge to slowly deflect the teeth 48 inwards when the tip of the hook 52 contacts an obstacle. The cantilever beam 50 and the hook 52 may be the same for each of the teeth 48, however in other embodiments a length, width, or thickness of one or more of the teeth 48 varies.

Figure 24:
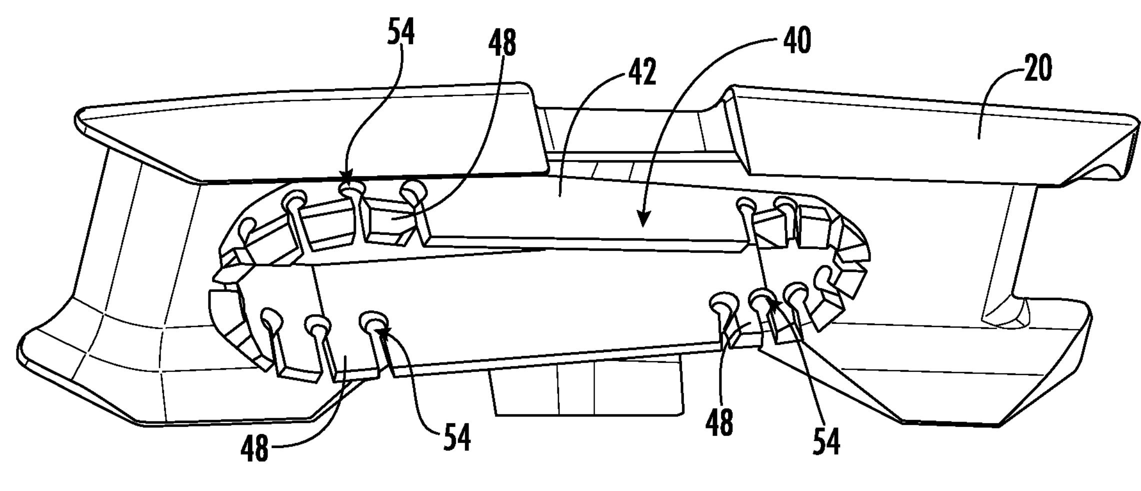
FIG. 24 is a bottom perspective view of a locking endplate of the implant of FIG. 21 according to an example embodiment.
Figure 25:
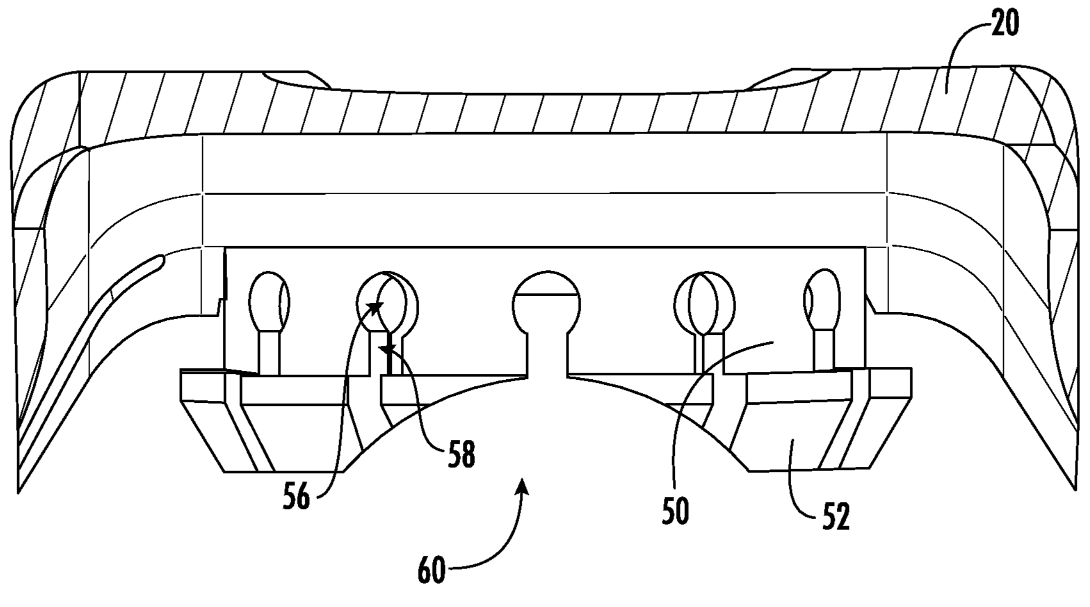
FIG. 25 is a cross-section of a locking endplate of the implant of FIG. 21 according to an example embodiment.
Figure 26:
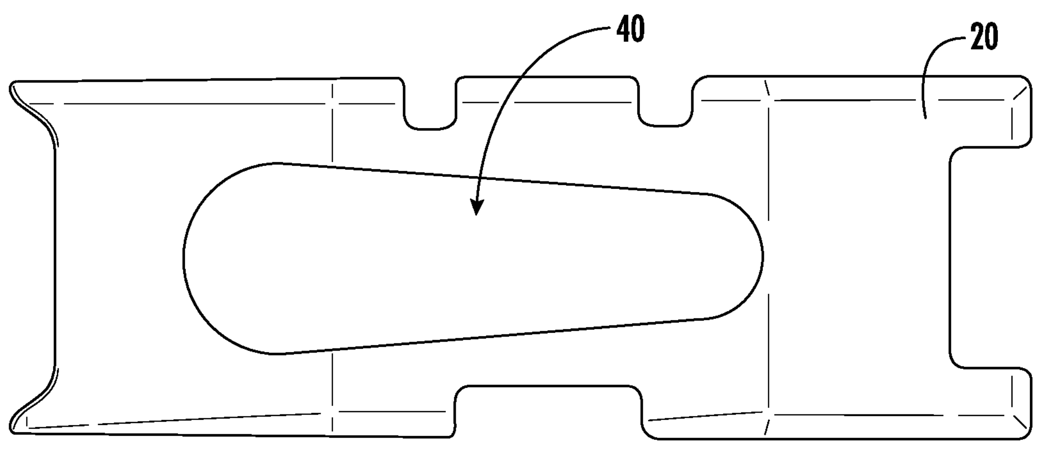
FIG. 26 is a top view of a locking endplate of the implant of FIG. 21 according to an example embodiment.

In some embodiments, the gaps 54 may be irregular or asymmetrically shaped, and the gaps 54 may be wider at a base of the gap closest to the endplates 20, 24 than at the end of the gap 54 furthest form the endplates 20, 24, wider at the further point and narrower at the base, or have a consistent gap distance throughout the length of the gap 54. For example, as shown in FIGS. 24 and 25, the gap 54 includes an aperture 56 and a channel 58. The channel 58 extends from the aperture 56 and in some embodiments is narrower than the aperture 56. The aperture 56 can vary in size to adjust the amount of force required to deflect the teeth 48. In some embodiments, the aperture 56 is excluded and the channel 58 extends from a base of the gap 54 to an end of the gap 54.

In some embodiments, as discussed above when referring to FIG. 3, the protrusion 42 and/or the teeth 48 may include cut-outs (e.g., recesses, grooves, indents, etc.) to provide space for components of the control assembly 16 such as the control shaft 30. As shown in FIG. 25, the protrusion 42 and/or the teeth 48 includes such a cut-out in cut-out 60. Cut-out 60 is a semi-circular or substantially semi-circular to accommodate one or more other components of the implant 10.

Figure 27:
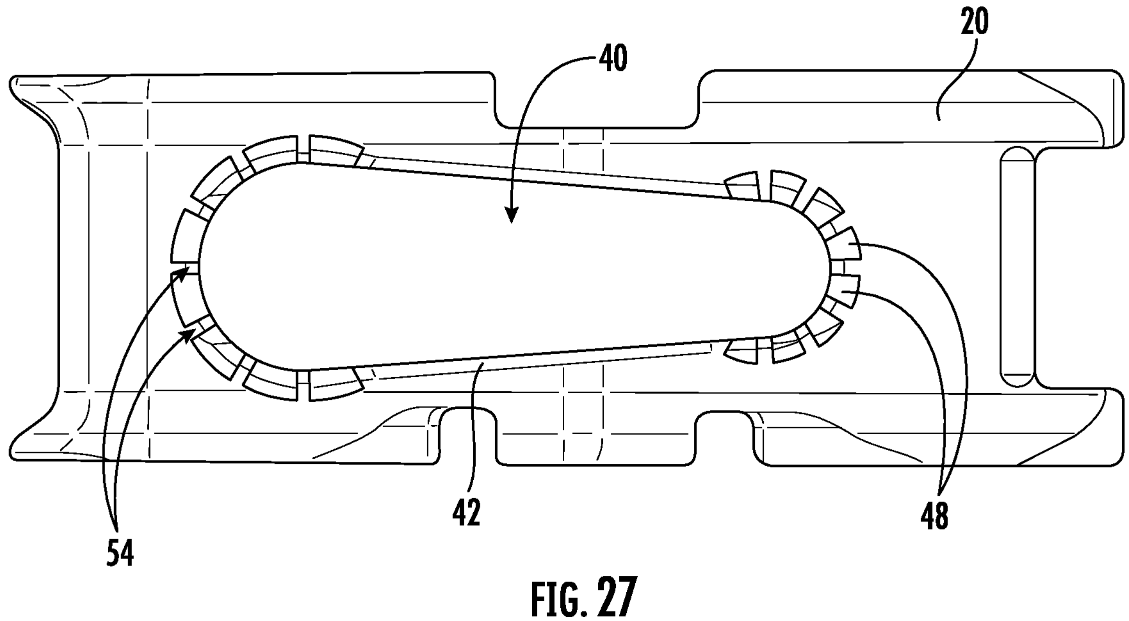
FIG. 27 is a bottom view of a locking endplate of the implant of FIG. 21 according to an example embodiment.

In some embodiments, for example referring to FIG. 27, the teeth 48 extend only partially around the perimeter of the projection 42/graft window 40 of the endplates 20, 24. In some embodiments, the teeth 48 may be grouped into one or more groups. Still in other embodiments the teeth 48 may extend around the entire perimeter of the graft window 40.

Figure 28:
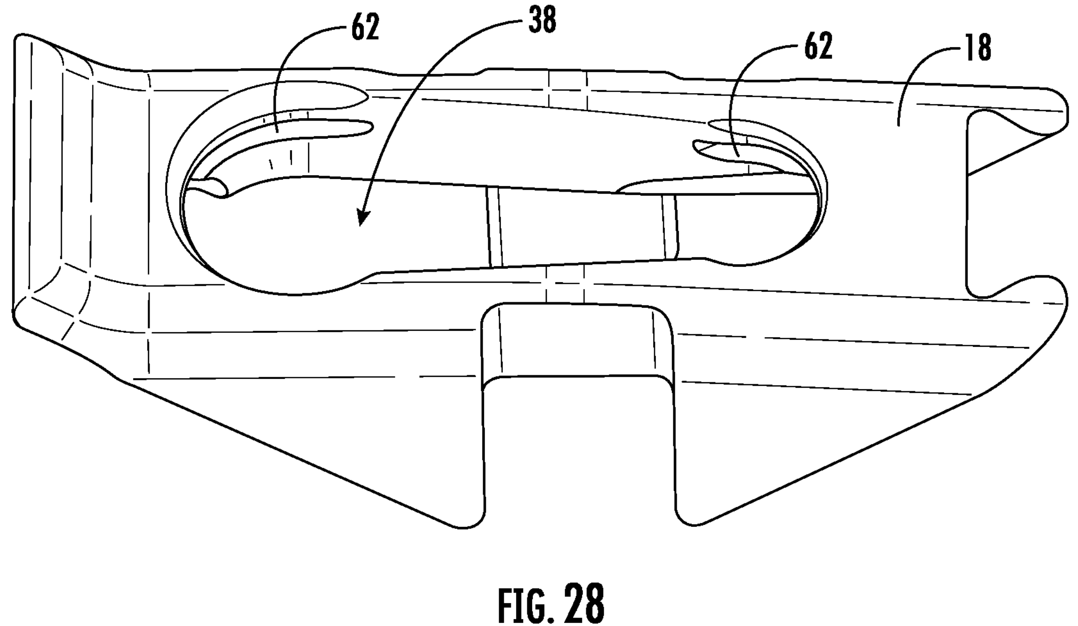
FIG. 28 is a top perspective view of an upper base member of the implant of FIG. 21 according to an example embodiment.
Figure 29:
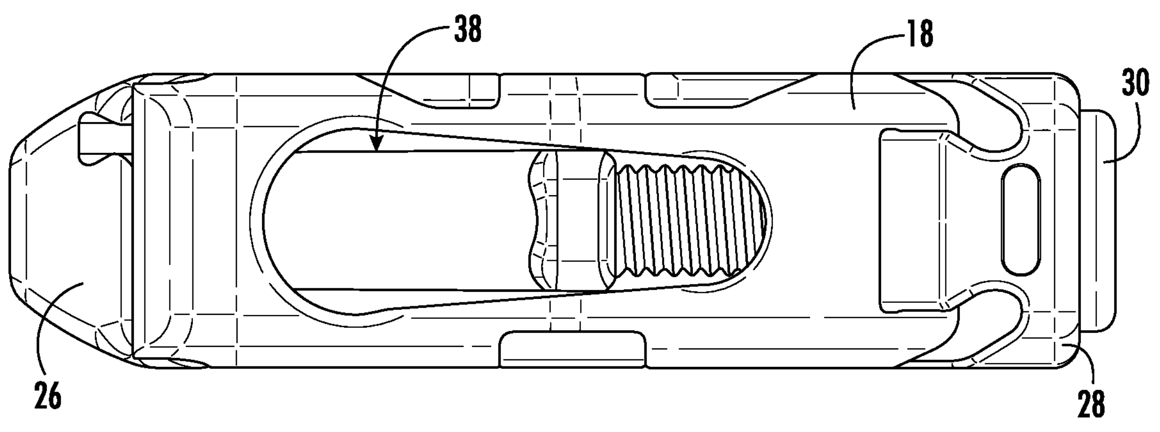
FIG. 29 is a top view of an upper base member of the implant of FIG. 21 according to an example embodiment.
Figure 30:
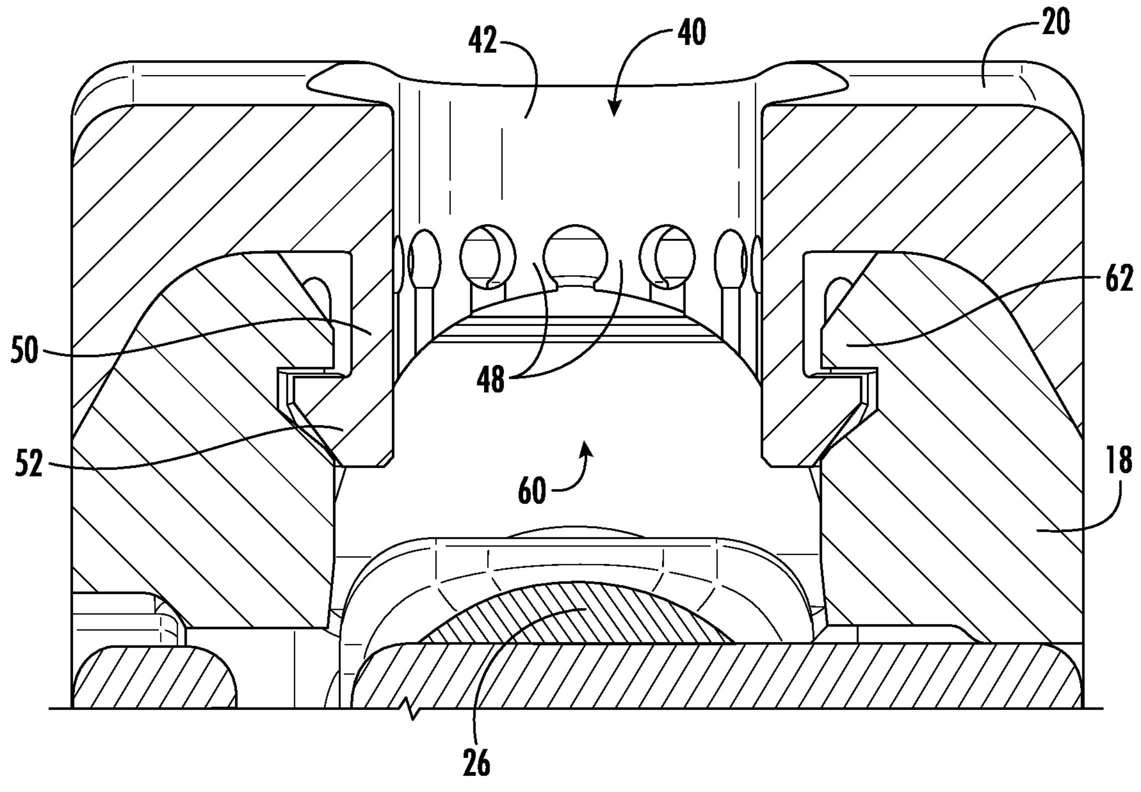
FIG. 30 is a cross-section of the implant of FIG. 21 according to an example embodiment.

Referring now to FIGS. 28 and 29, the base members 18, 22 include graft windows 38 to receive the teeth 48 of the endplates 20, 24. The graft window 38 is substantially the same shape as the graft window 40 and the protrusion 42. In some embodiments, the graft window 38 is larger than the graft window 40 to accommodate the hooks 52 of the teeth 48. The graft window 38 includes a small lateral protrusion or ledge shown as ridges 62 along the perimeter of the graft window 38. The ridges define a recess (e.g., void, space, etc.). The ridges 62 extend into the graft window 38. A user, when attaching the endplates 20, 24 to the base members 18, 22 pushes the endplates 20, 24 down such that the protrusion 42 engages with the ridges 62. The sloped hooks 52 of the teeth 48 engage the ridges 62 and deflect inwards as the endplates 20, 24 are brought into contact with the base members 18, 22. Once the teeth 48 pass the ridges 62 the teeth 48 bend back to interlock with the ridges 62 and secure the endplates 20, 24 to the base members 18, 22. For example, FIG. 30 illustrates a cross-section of the implant 10. The hooks 52 of the teeth 48 are underneath and engaged with the ridges 62 to inhibit the endplate 20 from separating from the base member 18. In some embodiments, the ridge 62 includes a channel or gap beneath it to accommodate the teeth 52. The channel can be sized to match an angle or slope of the hooks 52. The ridges 62 may also be sloped or angled like the hooks 52 to facilitate the deflection of the teeth 48 while reducing friction and the amount of force required to engage the endplates 20, 24 with the base members 18, 22.

Figure 35:
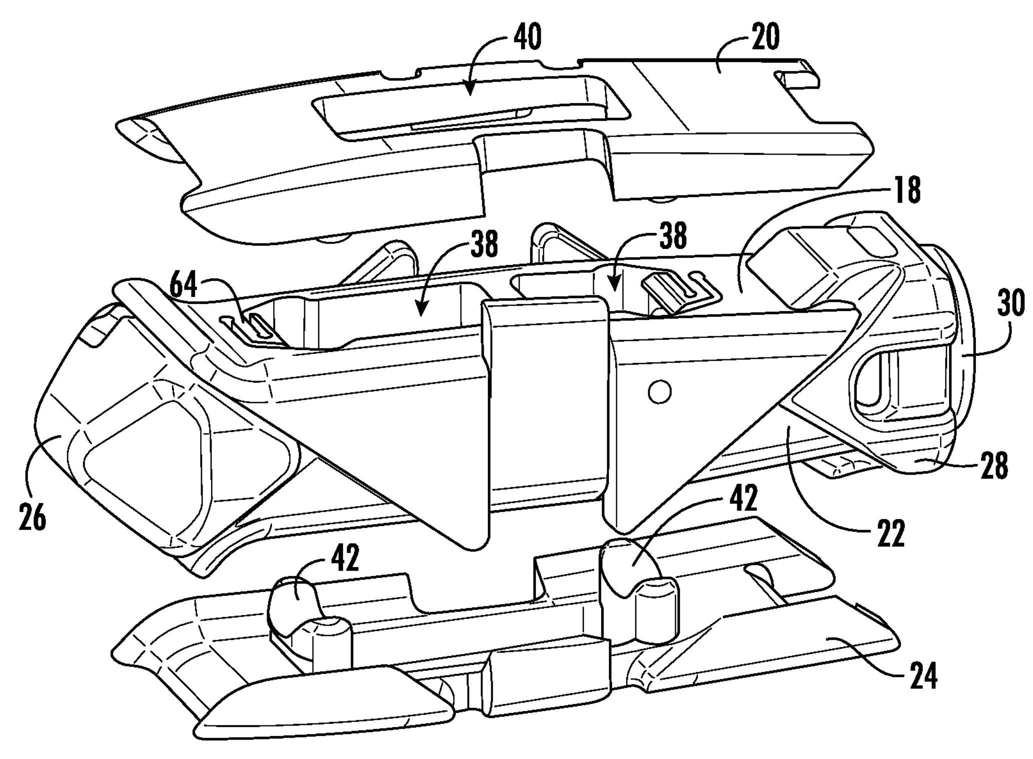
FIG. 35 is a partially exploded view of the implant of FIG. 34 according to an example embodiment.
Figure 36:
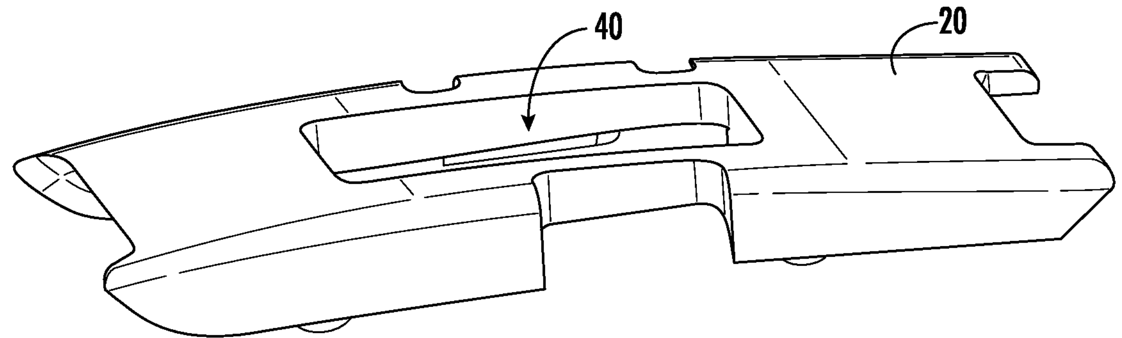
FIG. 36 is a top view of an upper endplate of the implant of FIG. 34 according to an example embodiment.
Figure 37:
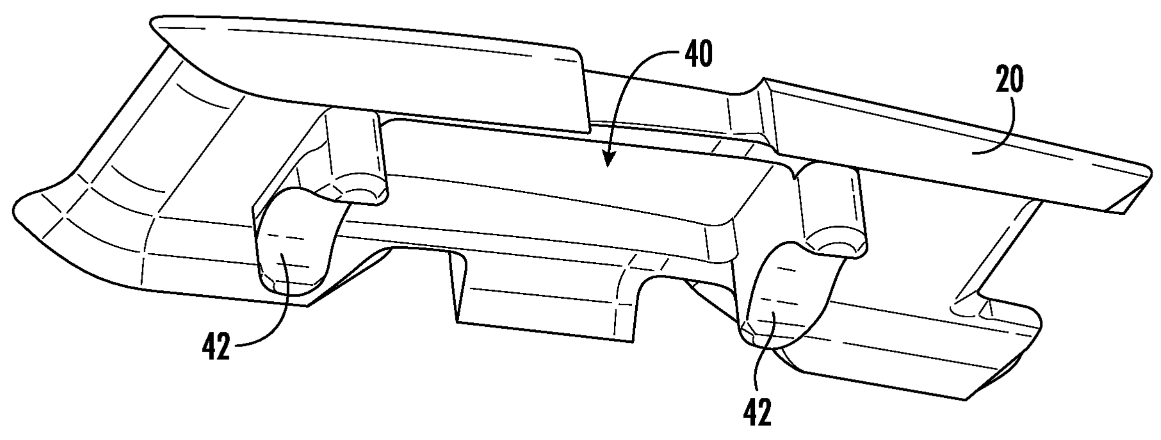
FIG. 37 is a bottom perspective view of an upper endplate of the implant of FIG. 34 according to an example embodiment.

In some embodiments, the securement features are reversed, such that the base members 18, 22 include the flexible or moving securement features in addition and/or alternatively to the endplates 20, 24. For example, referring to FIGS. 34-39, the base members 18, 22 include snap-fit elements 64 which engage with protrusions 42 of the endplates 20, 24 for securing the endplates 20, 24 to the base members 18, 22. As shown in FIGS. 35-37, the endplates 20, 24 include one or more protrusions 42 extending down and away from the endplate 20, 24. The protrusions 42 may be positioned at one or more ends of the graft window 40 of the endplates 20, 24. In some embodiments, the protrusions 42 engage with the sides of the graft windows 38 to orient and align the endplates 20, 24 with the base members 18, 22. In some embodiments, the protrusions 42 have a cut-out to accommodate the control assembly 16. In some embodiments, for example with reference to FIGS. 42 and 43, the protrusions 42 terminate in hooks 52.

Figure 38:
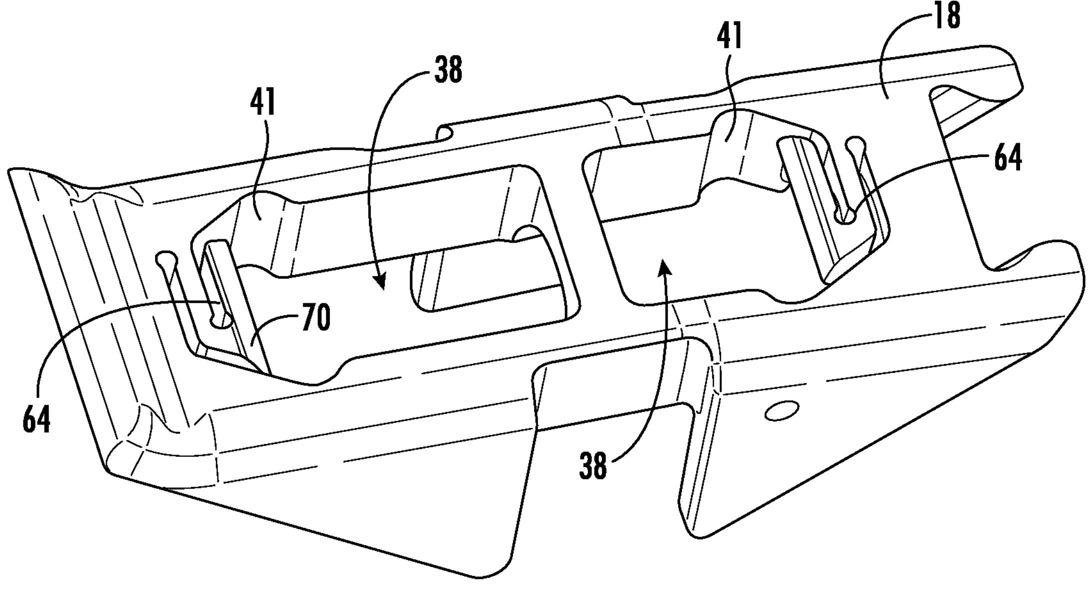
FIG. 38 is a perspective view of a locking upper base member of the implant of FIG. 34 according to an example embodiment.
Figure 39:
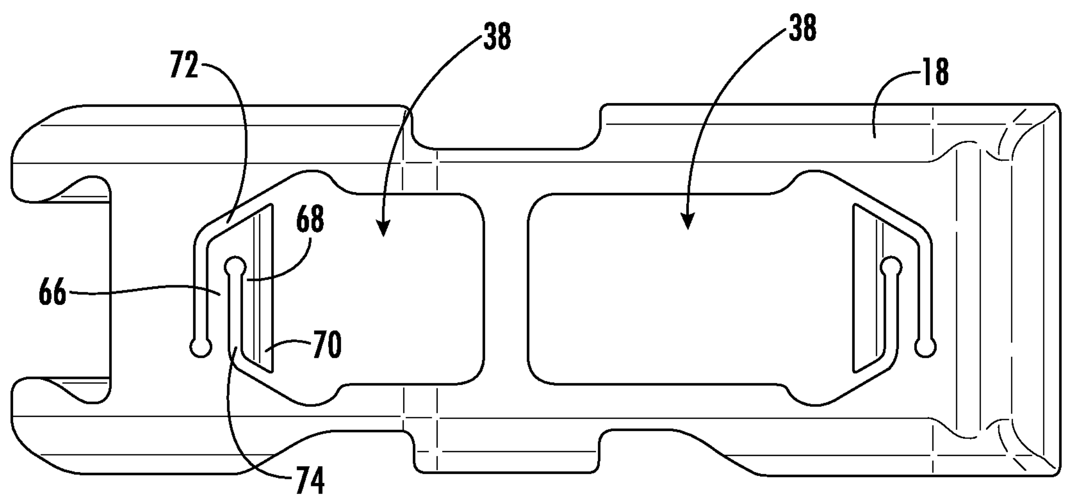
FIG. 39 is a top view of a locking upper base member of the implant of FIG. 34 according to an example embodiment.
Figure 40:
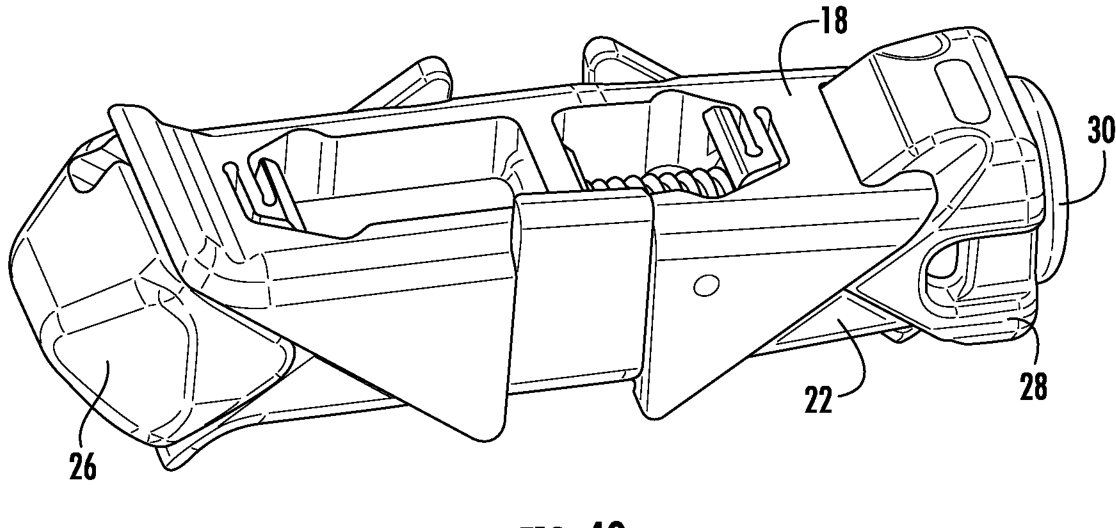
FIG. 40 is a perspective view of the implant of FIG. 34 without the upper and lower endplates according to an example embodiment.
Figure 41:
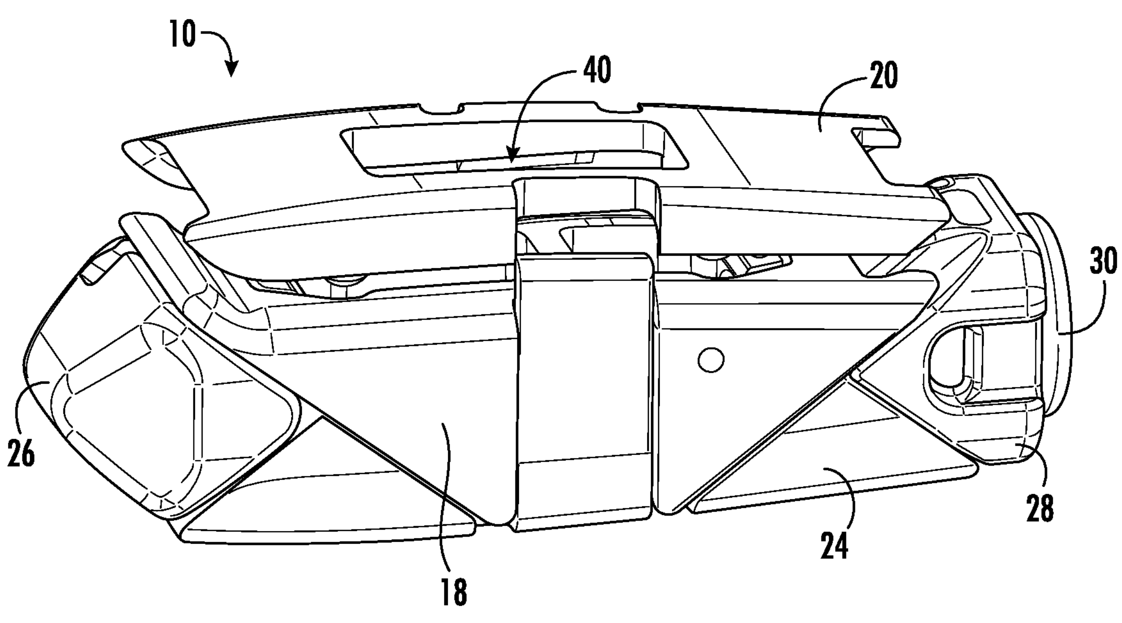
FIG. 41 is a partially exploded view of the implant of FIG. 34 with the upper endplate detached according to an example embodiment.

Referring now to FIGS. 38 and 39, the base members 18, 22 are shown including snap-fit elements 64 extending within each graft window 38. The base members 18, 22 can include one or more graft windows 38, which together can correspond to one or more graft windows 40 in the endplate 20, 24. The snap-fit elements 64 include cantilever beams 66, 68. An angled engagement surface 70 extends away from the cantilever beam 68 at its highest point until it terminates down at its lowest point. In some embodiments, there may be more or fewer than two cantilever beams 66, 68 in the snap-fit elements 64. The cantilever beams 66, 68 are separated from each other and the base members 18, 22 by gaps 72, 74. The gaps 72, 74 allow the cantilever beams 66, 68 to deflect outwards away from a center of the graft window 38. The cantilever beams 66, 68 are composed of an elastically flexible material to allow the cantilever beams 66, 68 to deflect and bend back to their original shape.

Figure 42:
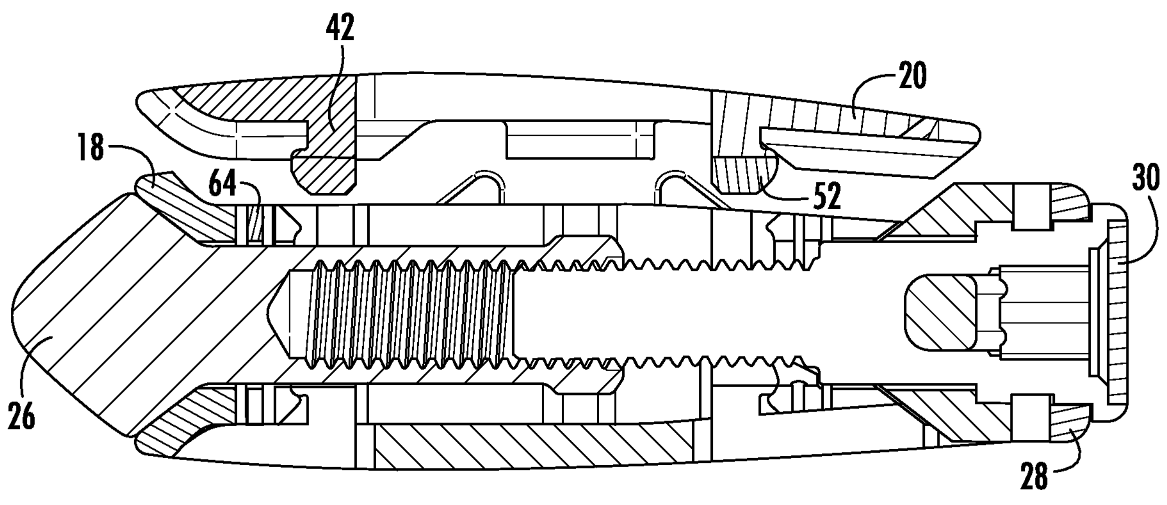
FIG. 42 is a cross-section of the implant of FIG. 34 with the upper endplate detached according to an example embodiment.
Figure 43:
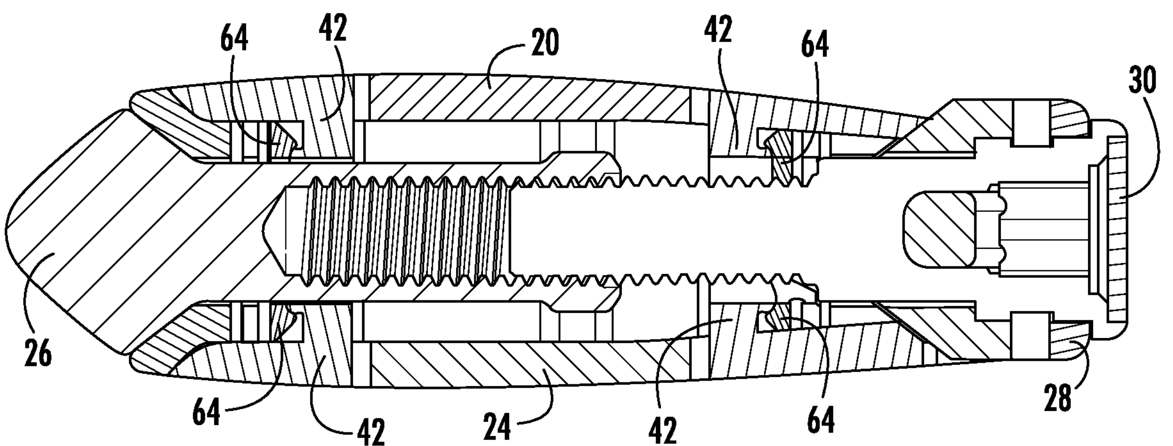
FIG. 43 is a cross-section of the implant of FIG. 35 with the upper endplate attached according to an example embodiment.

In operation, as shown in FIGS. 40-43, the base members 18, 22 engage with the control assembly 16 and then the endplates 20, 24 are secured to the base members 18, 22 through the interlocking of the snap-fit elements 64 and the protrusions 42. Referring specifically to FIGS. 42 and 42, the hooks 52 at the ends of the protrusions 42 of the of the endplates 20, 24 extend down through the graft windows 38 of the base members 18, 22. The protrusions 42 engage with the sides of the graft windows 38 to align and orient the endplates 20, 24. The protrusions 42 thereby ensure vertical loading is applied to the snap-fit elements 64 and reduce binding during assembly of the components. The angled surface of the hooks 52 contacts the angled slop 70 of the snap-fit element 64 causing the cantilever beams 66, 68 to deflect and be pushed out away from the hooks 52. Once the hooks 52 pass the slopped surface 70 the cantilever beams 66, 68 extend back to their original position and the slopped surface 70 interlocks with the hook 52 as shown in FIG. 43 to secure the endplates 20, 24 to the base members 18, 22.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on hardware systems chosen and on designer choice. All such variations are within the scope of the disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present application.

It should be appreciated that dimensions of the components, structures, and/or features of the present implants and installation instruments may be altered as desired within the scope of the present disclosure.

What is claimed is:

1. An expandable implant assembly, comprising:
- an upper endplate assembly configured to engage bone, the upper endplate assembly comprising:
  - an upper base member; and
  - a plurality of upper endplates, wherein each of the plurality of upper endplates is selectively coupleable to the upper base member;
  - wherein the upper base member comprises a first graft window, and wherein at least one of the plurality of upper endplates comprises a second graft window configured to be aligned with the first graft window when the at least one of the plurality of upper endplates is coupled to the upper base member;
- a lower endplate assembly configured to engage bone, the lower endplate assembly comprising:
  - a lower base member; and
  - a plurality of lower endplates, wherein each of the plurality of lower endplates is selectively coupleable to the lower base member; and
- a control assembly configured to couple the upper endplate assembly to the lower endplate assembly and control movement of the upper endplate assembly relative to the lower endplate assembly.

2. The assembly of claim 1, wherein each of the plurality of upper endplates is different from a remainder of the plurality of upper endplates in at least one of a height, width, material, and an angulation.

3. The assembly of claim 2, wherein each of the plurality of lower endplates is different from the remainder of the plurality of lower endplates in at least one of a height, width, material, and an angulation.

4. The assembly of claim 1, wherein the at least one of the plurality of upper endplates comprises a columnar structure defining the second graft window and extending into the first graft window.

5. The assembly of claim 4, wherein the columnar structure comprises a first securement feature configured to engage a second securement feature provided on the upper base member to secure the at least one of the plurality of upper endplates to the upper base member.

6. The assembly of claim 1, wherein at least one of the plurality of upper endplates or plurality of lower endplates is 3D printed.

7. The assembly of claim 6, wherein the at least one of the plurality of upper endplates is a porous structure intended to facilitate bone growth in and/or around the at least one of the plurality of upper endplates.

8. The assembly of claim 1, wherein each of the plurality of upper endplates and each of the plurality of lower endplates includes a projection configured to engage ridges in the base members in a snap-fit engagement.

9. The assembly of claim 1, wherein at least one of the plurality of upper endplates or plurality of lower endplates comprises asymmetrical apertures.

10. The assembly of claim 1, wherein at least one of the plurality of upper endplates or plurality of lower endplates comprises a non-planar lower surface configured to provide gaps between the at least one of the plurality of upper endplates or plurality of lower endplates endplate and base member.

11. The assembly of claim 1, wherein the upper base member comprises a lip on a distal end such that during insertion of the assembly the lip forms a leading edge for one of the plurality of upper endplates coupled to the upper base member.

12. The assembly of claim 1, wherein the control assembly comprises:

a proximal wedge member configured to engage proximal ends of the plurality of upper and plurality of lower endplate assemblies;

a distal wedge member configured to engage distal ends of the plurality of upper and plurality of lower endplate assemblies; and a control shaft coupled to the proximal and distal wedge members such that manipulation of the control shaft adjusts a distance between the proximal and distal wedge assemblies and a height of the expandable implant assembly.

13. An expandable implant assembly, comprising:

a first endplate assembly configured to engage bone, the first endplate assembly comprising:

a first base member; and a first modular endplate coupled to the first base member;

wherein the first base member includes an interior wall defining a first graft window and the first modular endplate includes a projection defining a second graft window, wherein the projection engages a ridge on the interior wall in a snap fit arrangement;

a second endplate assembly configured to engage bone, the second endplate assembly comprising:

a second base member; and a second modular endplate coupled to the second base member; and a control assembly configured to couple the first endplate assembly to the second endplate assembly and control movement of the first endplate assembly relative to the second endplate assembly.

14. The assembly of claim 13, wherein the first base member includes an interior wall defining a first graft window and a projection extending from the interior wall into the first graft window and the first modular endplate includes a protrusion extending from the first modular endplate, wherein the projection engages the protrusion in a snap fit engagement.

15. The assembly of claim 14, wherein at least one of the first base member or the first modular endplate is 3D-printed.

16. The assembly of claim 14, wherein the protrusion is a hook and wherein the projection deflects as the projection engages the hook.

17. A method of configuring an implant, comprising:

selecting an upper endplate from a plurality of upper endplates;

selecting a lower endplate from a plurality of lower endplates; and coupling the upper endplate to an upper base member and coupling the lower endplate to a lower base member to form an implant, the implant comprising:

an upper endplate assembly comprising the upper endplate and the upper base member;

a lower endplate assembly comprising the lower endplate and the lower base member;

a first graft window in the first base member;

a second graft window in the first endplate that is aligned with the first graft window when the first endplate is coupled to the first base member and a control assembly operatively coupling the upper endplate assembly to the lower endplate assembly and configured to control relative movement between the upper endplate assembly and the lower endplate assembly, the control assembly operatively couplable to at least two of the plurality of upper endplates and at least two of the plurality of lower endplates.

18. The method of claim 17, wherein coupling the upper endplate to the upper base member comprises a projection of the upper endplate engaging a ridge in the upper base member in a snap-fit engagement.

* * * * *